(12) United States Patent
Wang et al.

(10) Patent No.: US 10,746,706 B2
(45) Date of Patent: Aug. 18, 2020

(54) PHOTOACOUSTIC PHYSIO-CHEMICAL TISSUE ANALYSIS

(71) Applicant: The Regents of the University of Michigan, Ann Arbor, MI (US)

(72) Inventors: Xueding Wang, Ann Arbor, MI (US); Cheri Deng, Ann Arbor, MI (US); Paul L. Carson, Ann Arbor, MI (US); Guan Xu, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 736 days.

(21) Appl. No.: 15/108,717

(22) PCT Filed: Jan. 5, 2015

(86) PCT No.: PCT/US2015/010181
§ 371 (c)(1),
(2) Date: Jun. 28, 2016

(87) PCT Pub. No.: WO2015/103550
PCT Pub. Date: Jul. 9, 2015

(65) Prior Publication Data
US 2016/0327524 A1 Nov. 10, 2016

Related U.S. Application Data

(60) Provisional application No. 61/923,524, filed on Jan. 3, 2014.

(51) Int. Cl.
*G01N 29/24* (2006.01)
*G01N 29/06* (2006.01)
(Continued)

(52) U.S. Cl.
CPC ....... *G01N 29/2418* (2013.01); *A61B 5/0095* (2013.01); *G01N 21/1702* (2013.01);
(Continued)

(58) Field of Classification Search
CPC .......... G01N 29/2418; G01N 33/4833; G01N 29/0654; G01N 29/11; G01N 29/46;
(Continued)

(56) References Cited

U.S. PATENT DOCUMENTS 4,723,553 A 2/1988 Miwa et al.
5,446,681 A * 8/1995 Gethner ............... G01N 21/359
702/27

(Continued)

OTHER PUBLICATIONS

International Search Report and Written Opinion for PCT/US2015/010181, dated Apr. 30, 2015; ISA/KR.
(Continued)

*Primary Examiner* — Sanjay Cattungal
(74) *Attorney, Agent, or Firm* — Harness, Dickey & Pierce, P.L.C.

(57) ABSTRACT

A method of performing a photoacoustic physio-chemical analysis is provided. The method includes performing one or more photoacoustic scans on a tissue to generate a plurality of photoacoustic signals. The photoacoustic signals are transformed into a frequency domain to form a power spectra. The method also includes generating a two dimensional (2D) physio-chemical spectrogram from the power spectra. A probe for performing a photoacoustic physio-chemical analysis is also provided.

20 Claims, 20 Drawing Sheets

Figures 1A, 1B, 1C, 1D:
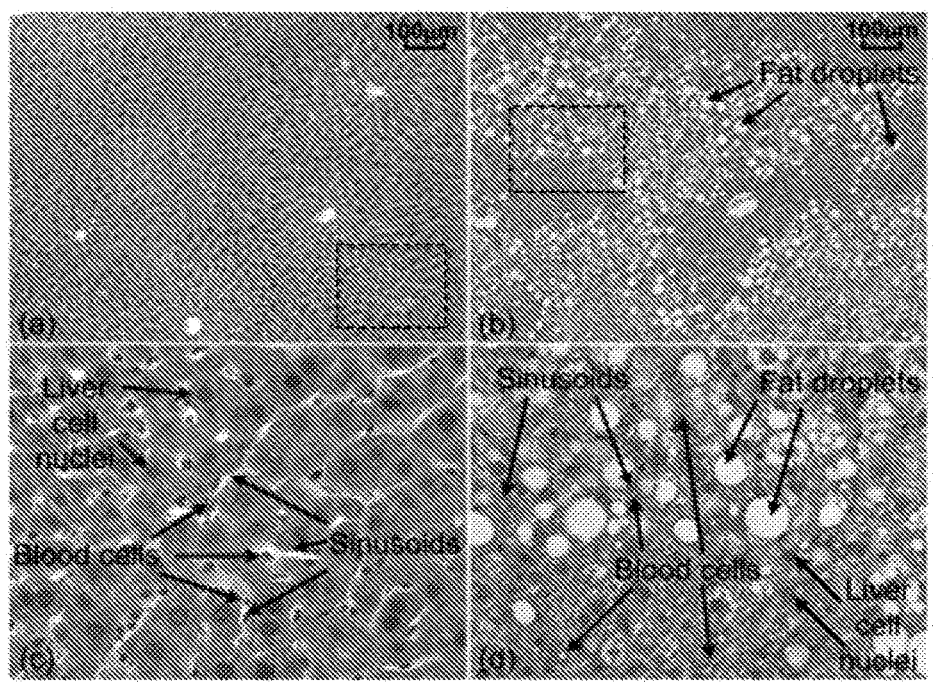

(51) Int. Cl.
  *A61B 5/00* (2006.01)
  *G01N 29/11* (2006.01)
  *G01N 29/46* (2006.01)
  *G01N 21/17* (2006.01)
  *G01N 33/483* (2006.01)
(52) U.S. Cl.
  CPC ......... *G01N 29/0654* (2013.01); *G01N 29/11* (2013.01); *G01N 29/46* (2013.01); *G01N 33/4833* (2013.01); *A61B 2503/40* (2013.01); *A61B 2503/42* (2013.01); *G01N 2021/1706* (2013.01); *G01N 2291/02475* (2013.01)
(58) Field of Classification Search
  CPC ....... G01N 21/1702; G01N 2021/1706; G01N 2291/02475; A61B 5/0095; A61B 2503/42; A61B 2503/40
  USPC ................................................ 600/437–480
  See application file for complete search history.

(56) References Cited

U.S. PATENT DOCUMENTS

| | | | | |
|---|---|---|---|---|
| 5,926,273 | A * | 7/1999 | Kimura | G01J 3/42 356/502 |
| 6,025,913 | A * | 2/2000 | Curbelo | G01J 3/447 250/339.08 |
| 7,864,307 | B2 | 1/2011 | Fukutani et al. | |
| 2004/0054268 | A1 | 3/2004 | Esenaliev et al. | |
| 2004/0128081 | A1 * | 7/2004 | Rabitz | G01N 21/636 702/23 |
| 2005/0151976 | A1 * | 7/2005 | Toma | A61B 5/0066 356/497 |
| 2005/0203419 | A1 | 9/2005 | Ramanujam et al. | |
| 2007/0043341 | A1 * | 2/2007 | Anderson | A61B 5/0059 606/12 |
| 2007/0106172 | A1 * | 5/2007 | Abreu | A61B 5/6821 600/549 |
| 2009/0105605 | A1 * | 4/2009 | Abreu | A61B 5/0008 600/549 |
| 2011/0054292 | A1 * | 3/2011 | Hirson | A61B 5/0073 600/407 |
| 2011/0098572 | A1 * | 4/2011 | Chen | A61B 5/0062 600/463 |
| 2012/0010541 | A1 | 1/2012 | Cain et al. | |
| 2012/0123256 | A1 | 5/2012 | Razansky et al. | |
| 2013/0039147 | A1 * | 2/2013 | Witte | A61B 5/0093 367/7 |
| 2013/0102865 | A1 | 4/2013 | Mandelis et al. | |
| 2013/0190591 | A1 * | 7/2013 | Hirson | A61B 5/0095 600/407 |
| 2015/0150464 | A1 * | 6/2015 | Boctor | A61B 5/0095 600/424 |
| 2015/0233811 | A1 * | 8/2015 | Strohm | G01N 15/14 73/601 |

OTHER PUBLICATIONS

Allen, Thomas J. et al., "Spectroscopic photoacoustic imaging of lipid-rich plaques in the human aorta in the 740 to 1400 nm wavelength range," Journal of Biomedical Optics, 17 (6), pp. 061209-1-061209-10 (Published online: May 7, 2012).

Kumon, Ronald E. et al., "Frequency-Domain Analysis of Photoacoustic Imaging Data from Prostate Adenocarcinoma Tumor in a Murine Model," Ultrasound Med. Biol. 37 (5), pp. 834-839( 2011); doi: 10.1016/j.ultrasmedbio.2011.01.012.

Wang, Xueding et al., "Noninvasive laser-induced photoacoustic tomography for structural and functional in vivo imaging of the brain," Nat Biotechnol. 21 (7), pp. 803-806; doi: 10.1038/nbt839 (Published online: Jun. 15, 2003).

Xie, Zhixing et al., "Combined Photoacoustic and Acoustic Imaging of Human Breasts Specimens in the Mammographic Geometry," Ultrasound Med. Biol. 39 (11), pp. 2176-2184 (2013); doi: 10.1016/j.ultrasmedbio.2013.05.018.

Xu, Guan et al., "Photoacoustic spectrum analysis for microstructure characterization in biological tissue: A feasibility study," Appl. Phys. Lett 101 (22) pp. 221102-221105; doi: 10.1063/1.4768703 (Published online: Nov. 26, 2012).

Cortes, Corinna and Vapnik, Vladimir, "Support-Vector Networks." Machine Learning, vol. 20, No. 3, pp. 273-297 (1995).

Harrison, Tyler et al., "Combined photoacoustic and ultrasound biomicroscopy." Optics Express, vol. 17, No. 24, pp. 22041-22046 (Nov. 2009).

Hyvärinen, A. and Oja, E., "Independent component analysis: algorithms and applications." Neural Networks, vol. 13, No. 4-5, pp. 411-430 (2000).

Johnson, Jami Lynne, "Toward characterization of diseased vascular structures using noncontact photoacoustic and laser-ultrasound imaging: a phantom study." Master's Thesis, Boise State University (May 2013).

Kolkman, Roy G. M. et al., "Real-time Photoacoustic & Ultrasound imaging of human vasculature." Photons Plus Ultrasound: Imaging and Sensing 2009, Proceedings of SPIE, vol. 7177, pp. 717704-1-717704-5 (2009).

Lizzi, Frederic L. et al., "Relationship of Ultrasonic Spectral Parameters to Features of Tissue Microstructure." IEEE Transactions on Ultrasonics, Ferroelectrics, and Frequency Control, vol. 34, No. 3, pp. 319-329 (May 1987).

Lizzi, Frederic L. et al., "Statistical framework for ultrasonic spectral parameter imaging." Ultrasound in Medicine and Biology, vol. 23, No. 9, pp. 1371-1382 (1997).

Lizzi, Frederic L. et al., "Ultrasonic spectrum analysis for tissue assays and therapy evaluation." International Journal of Imaging Systems and Technology, vol. 8, No. 1, pp. 3-10 (1997).

Montilla, Leonardo G. et al., "Real-time photoacoustic and ultrasound imaging: a simple solution for clinical ultrasound systems with linear arrays." Physics in Medicine and Biology, vol. 58, pp. N1-N12 (2013).

Ossant, Frédéric et al., "Ultrasonic characterization of maturation of fetal lung microstructure: an animal study." Ultrasound in Medicine and Biology, vol. 27, No. 2, pp. 157-169 (Feb. 2001).

Sethuraman, Shriram et al., "Spectroscopic intravascular photoacoustic imaging to differentiate atherosclerotic plaques." Optics Express, vol. 16, No. 5, pp. 3362-3367 (Mar. 2008).

Steinberg, Idan et al., "Multispectral photoacoustic method for the early detection and diagnosis of osteoporosis." Photonic Therapeutics and Diagnostics IX, Proceedings of SPIE, vol. 8565, pp. 85656G-1-85656G-9 (2013).

Sun, Yang et al., "Development of a Multi-modal Tissue Diagnostic System Combining High Frequency Ultrasound and Photoacoustic Imaging with Lifetime Fluorescence Spectroscopy." Proceedings of the IEEE Ultrasonics Symposium, No. 10547261, pp. 570-573 (2008).

Sun, Yang et al., "Multimodal characterization of compositional, structural and functional features of human atherosclerotic plaques." Biomedical Optics Express, vol. 2, No. 8, pp. 2288-2298 (Aug. 2011).

Sun, Yao et al., "Photoacoustic Imaging: An Emerging Optical Modality in Diagnostic and Theranostic Medicine." Biosensors & Bioelectronics, vol. 2, No. 3, pp. 1000108-1-1000108-12 (2011).

Wang, Han-Wei et al., "Label-Free Bond-Selective Imaging by Listening to Vibrationally Excited Molecules." Physical Review Letters, vol. 106, No. 23, pp. 238106-1-238106-4 (Jun. 2011).

Wang, Lihong V., "Multiscale photoacoustic microscopy and computed tomography." Nature Photonics, vol. 3, No. 9, pp. 503-509 (Sep. 2009).

Wang, Pu et al., "Mapping lipid and collagen by multispectral photoacoustic imaging of chemical bond vibration." Journal of Biomedical Optics, vol. 17, No. 9, pp. 096010-1-096010-5 (Sep. 2012).

(56) References Cited

OTHER PUBLICATIONS

Wang, Shaohua et al., "Quantitative detection of stochastic microstructure in turbid media by photoacoustic spectral matching." Applied Physics Letters, vol. 102, No. 11, pp. 114102-1-11411024 (2013).

Wang, Xueding et al., "Noninvasive imaging of hemoglobin concentration and oxygenation in the rat brain using high-resolution photoacoustic tomography." Journal of Biomedical Optics, vol. 11, No. 2, pp. 024015-1-024015-9 (2006).

Wang, Xueding et al., "Three-dimensional laser-induced photoacoustic tomography of mouse brain with the skin and skull intact." Optics Letters, vol. 28, No. 19, pp. 1739-1741 (Oct. 2003).

Welch, Peter D., "The Use of Fast Fourier Transform for the Estimation of Power Spectra: A Method Based on Time Averaging Over Short, Modified Periodograms." IEEE Transactions on Audio and Electroacoustics, vol. AU-15, No. 2, pp. 70-73 (Jun. 1967).

Xu, Chen et al., "Investigation of a quantitative photoacoustictomography fitting procedure on multiple targets in reflection geometry with diffuse optical measurement assistance." Photons Plus Ultrasound: Imaging and Sensing 2012, Proceedings of SPIE, vol. 8223, pp. 822349-1-822349-11 (2012).

Xu, Guan et al., "The Functional Pitch of an Organ: Quantification of Tissue Texture with Photoacoustic Spectrum Analysis." Radiology, vol. 271, No. 1, pp. 248-254 (Apr. 2014).

Yang, Yiqun et al., "Photoacoustic tomography of tissue subwavelength microstructure with a narrowband and low frequency system." Applied Physics Letters, vol. 101, No. 3, pp. 034105-1-034105-5 (2012).

Yao, Lei et al., "Quantitative photoacoustic tomography based on the radiative transfer equation." Optics Letters, vol. 34, No. 12, pp. 1765-1767 (2009).

Yuan, Jie et al., "Real-time photoacoustic and ultrasound dual-modality imaging system facilitated with graphics processing unit and code parallel optimization." Journal of Biomedical Optics, vol. 18, No. 8, pp. 086001-1-086001-5 (Aug. 2013).

Zhang, Hao F. et al., "Functional photoacoustic microscopy for high-resolution and noninvasive in vivo imaging." Nature Biotechnology, vol. 24, No. 7, pp. 848-851 (Jul. 2006).

* cited by examiner

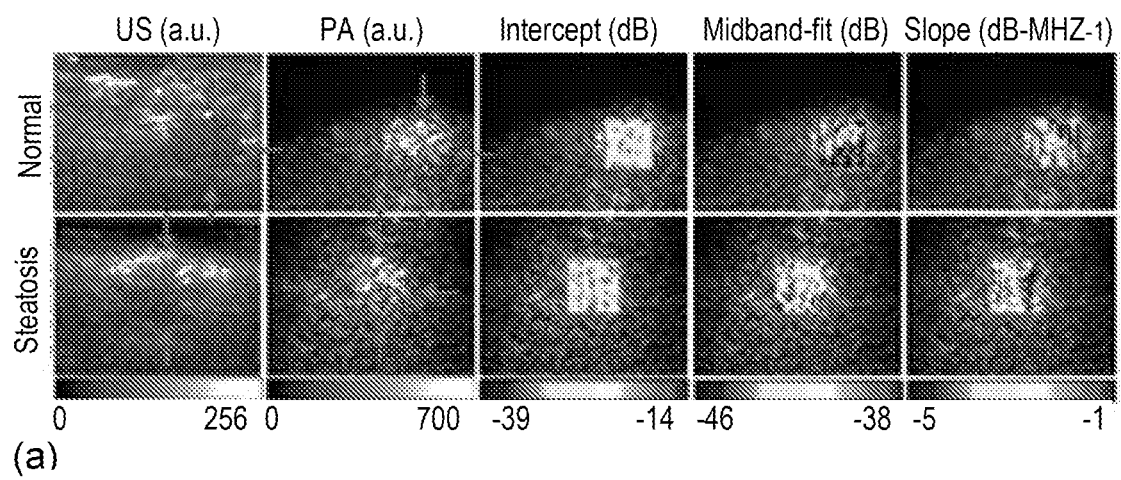
(a)
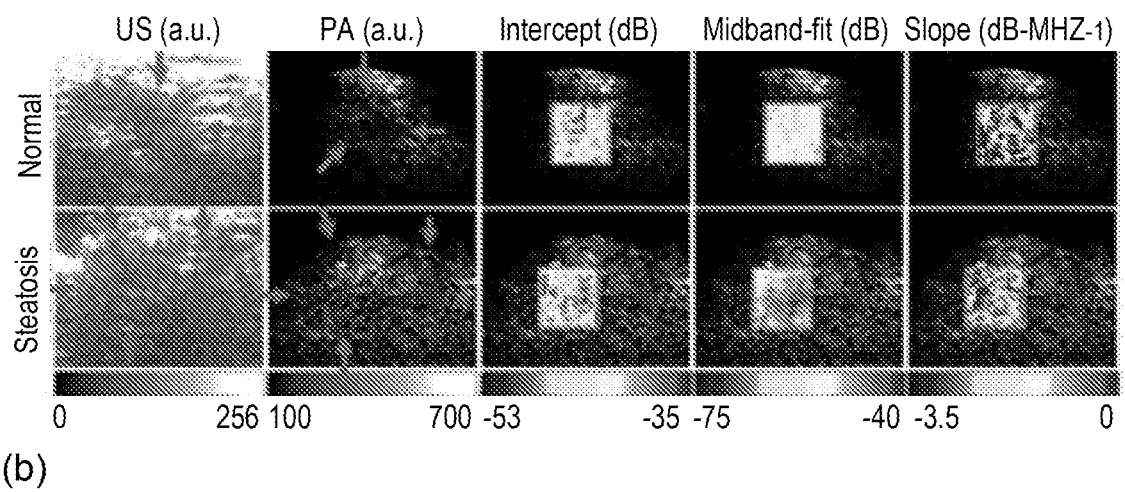
(b)
FIG. 14a – 14b
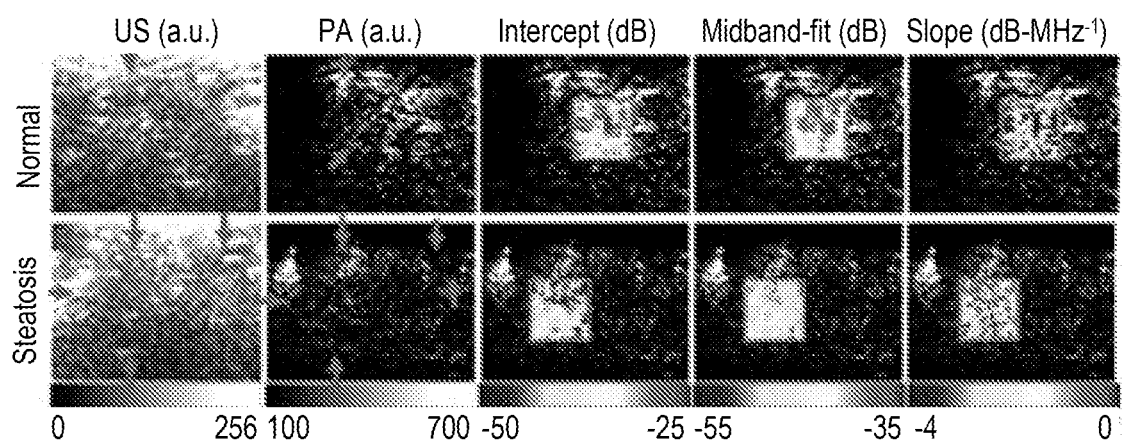
FIG. 15

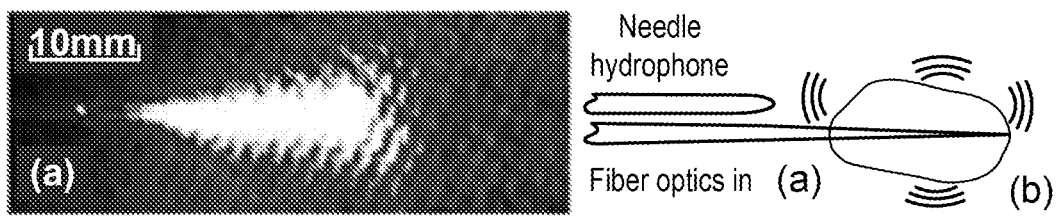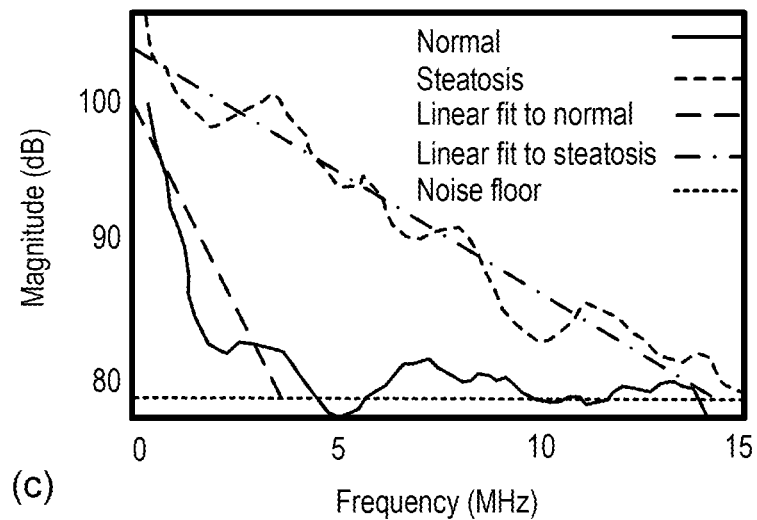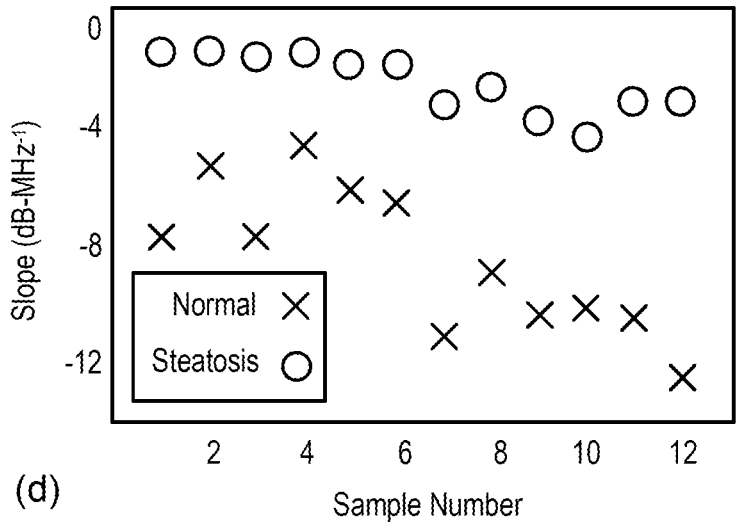
FIGS. 18a – 18d

PHOTOACOUSTIC PHYSIO-CHEMICAL TISSUE ANALYSIS

CROSS REFERENCE TO RELATED APPLICATIONS

This application is a U.S. National Phase Application under 35 U.S.C. 371 of International Application No. PCT/US2015/010181 filed on Jan. 5, 2015 and published as WO 2015/103550 A1 on Jul. 9, 2015, which claims the benefit of priority from U.S. Provisional Application No. 61/923,524 filed on Jan. 3, 2014. The entire disclosures of all of the above applications are incorporated herein by reference.

GOVERNMENT RIGHTS

This invention was made with government support under AR060350 awarded by the National Institutes of Health. The Government has certain rights in the invention.

FIELD

The present disclosure relates to medical imaging devices and methods for facilitating objective assessments of both physical and chemical biomarkers of tissues, including assessment of diseases in tissue in vivo.

BACKGROUND

This section provides background information related to the present disclosure which is not necessarily prior art.

Photoacoustic imaging (PAI) technology, one of the most rapidly growing areas in medical imaging in the last decade, shows great potential for improved diagnosis, monitoring, and treatment of many diseases. Relying on the detection of ultrasonic signals generated by laser illumination on biological samples, PAI is able to achieve high-resolution in optically scattering biologic tissues at relatively large depths. The majority of previous studies on PAI are focused on total signal magnitudes as an indication of macroscopic optical absorption by specific chemical components at single or multiple optical wavelengths. However, because of the limited bandwidth in photoacoustic (PA) signal detection, and the uncertainty of light fluence in tissue, conventional PAI images remain largely qualitative. Moreover, PAI findings are highly dependent on the individual system and operator, and hence, are difficult to be reproduced and used for purposes of objective comparison.

The extensive study on frequency domain analysis of radio frequency (RF) ultrasound (US) signals, e.g., US spectrum analysis (USSA) as a quantitative US technology, has shown potential for evaluating several parameters (such as dimension and density) of microscopic backscatters in biologic tissues. USSA has been explored for many years for its capability to detect and characterize diseases, including non-alcoholic fatty liver disease (NAFLD). USSA, however, is a purely "physical" imaging technique due to its mono-physics nature. Evaluating physical parameters of microscopic backscatters in tissue without interrogating the molecular components or chemical substances forming these backscattering micro-features has limited not only its specificity, but also its sensitivity for diagnosis. For example, a change in US backscattering in liver may not be a result of fat accumulation in liver cells, but instead due to the large amount of collagenous fiber depositing in the extra-cellular spaces, e.g., liver fibrosis. It has also been reported that US cannot be reliably used for early detection, because US is less sensitive to mild fatty liver and cannot detect NAFLD reliably until the degree of steatosis is above 33%.

Due to the physical-limiting nature of PAI and the chemical-limiting nature of USSA, there remains a need to develop an imaging system that can analyze both physical and chemical biological structures simultaneously.

SUMMARY

This section provides a general summary of the disclosure, and is not a comprehensive disclosure of its full scope or all of its features.

The present technology provides for a method of assessing physical and chemical biomarkers in a tissue. The method includes performing a photoacoustic scan by illuminating the tissue to generate acoustic signals and detecting the acoustic signals generated from the tissue. The method also includes transforming the acoustic signals into a plurality of frequency domains to create a plurality of power spectra and generating a two dimensional physio-chemical spectrogram (PCS) from the plurality of power spectra acquired from the photoacoustic scan.

The present technology also provides for a method of assessing physical chemical biomarkers in tissue of a liver. The method includes illuminating a region of a liver with a pulsed laser that is tunable over a broad wavelength range. For example, the wavelength range can be 680-950 nm and 1200-1700 nm. The method also includes detecting photoacoustic signals generated by the liver at each wavelength in the entire wavelength range. The method then includes transforming the photoacoustic signals into a frequency domain to create power spectra and generating a two dimensional physio-chemical spectrogram (PCS) map from the power spectra.

Additionally, the present technology provides for a method of performing photoacoustic physio-chemical analysis (PAPCA) on a tissue. The method includes performing a plurality of photoacoustic scans on a tissue to generate photoacoustic signals, wherein each scan comprises a broad range of wavelengths. The method further includes transforming the photoacoustic signal at each wavelength into a frequency domain to create power spectra, and generating a two dimensional physio-chemical spectrogram (PCS) from the power spectra. The PCS comprises a first axis representing an optical wavelength and a second axis representing ultrasonic frequency. The axis presenting the optical wavelength indicates the chemical components in the tissue. The ultrasonic frequency indicates the micron scale tissue features, such as whether the tissue is homogeneous or heterogeneous. The PCS provides physical and chemical information about the tissue simultaneously, which can be used to diagnosis diseases.

Also, the present technology provides a probe for PAPCA. The probe has a longitudinal body that defines an outer surface and a longitudinal core. The body terminates at a tip. The probe also includes an optical fiber extending longitudinally along the longitudinal core, a hydrophone positioned within the longitudinal core parallel to the optical fiber, and a window extending longitudinally along the body from a first end at or near the tip to a second end that is a predetermined distance (e.g., L) from the first end.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1(a)-1(d): 1(a) shows the histology of normal liver tissue and 1(b) shows fatty liver tissue. Magnified photographs of the areas marked by the dashed boxes in 1(a) and 1(b) are shown in 1(c) and 1(d), respectively.

Figure 2:
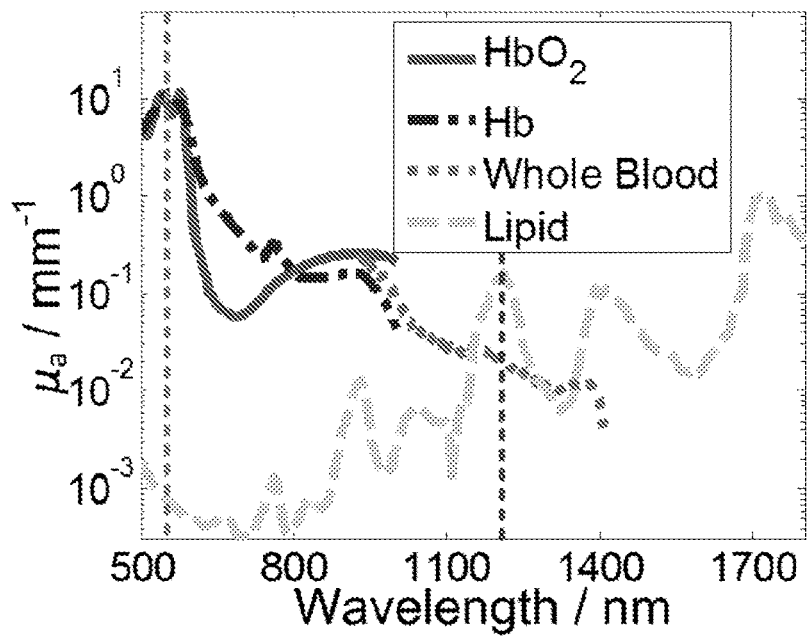

FIG. 2: shows the molecular vibrational absorption peak of the carbon-hydrogen bond in a lipid molecule at a wavelength of approximately 1200 nm and the hemoglobin absorption spectrum peak at a wavelength of approximately 532 nm.

Figure 3A:
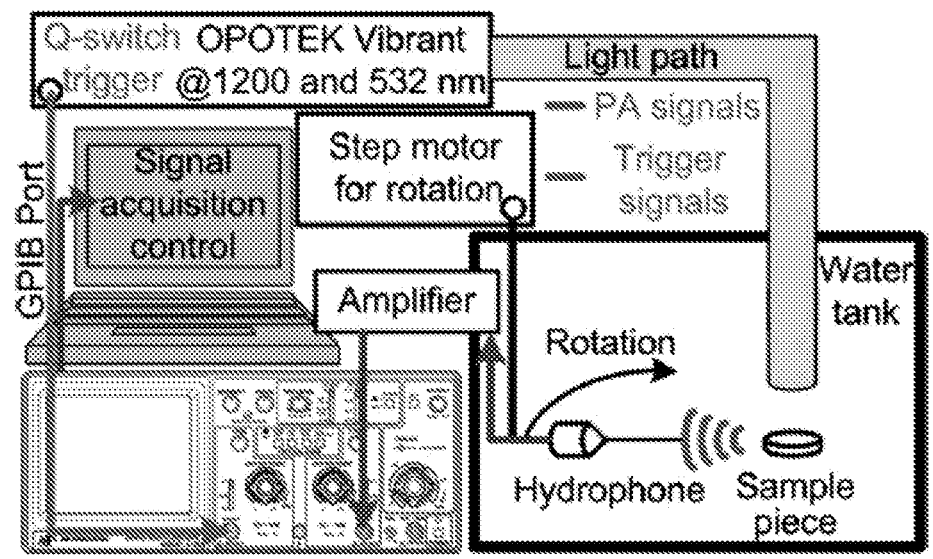
Figure 3B:
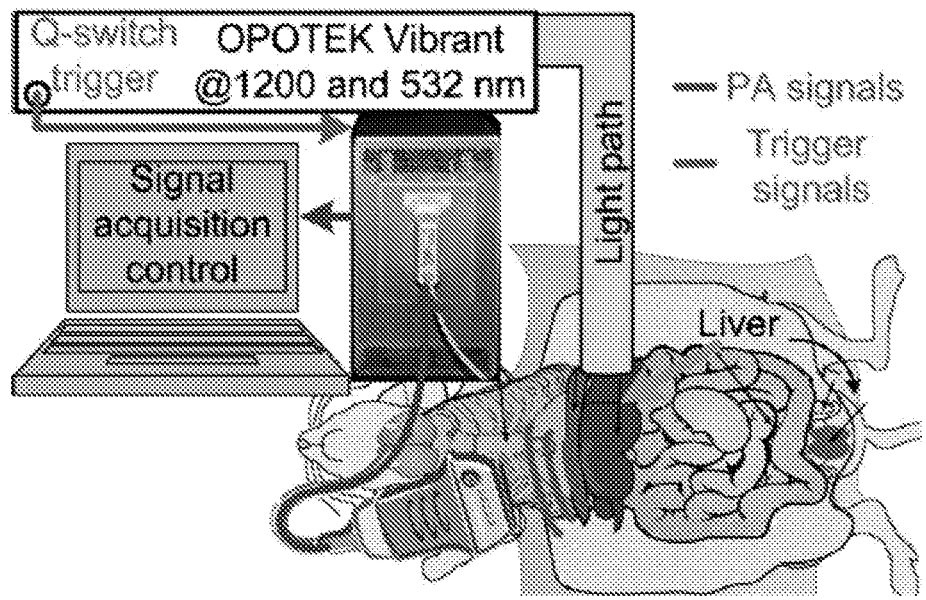

FIGS. 3(a)-3(b): experimental setups for an ex vivo imaging 3(a) and in situ imaging 3(b) of mouse liver.

Figure 4A:
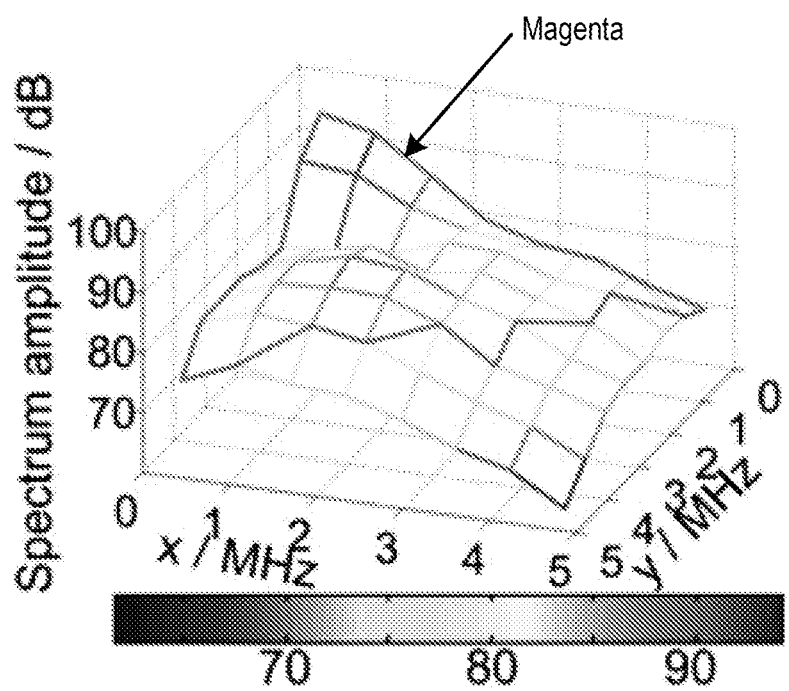
Figure 4B:
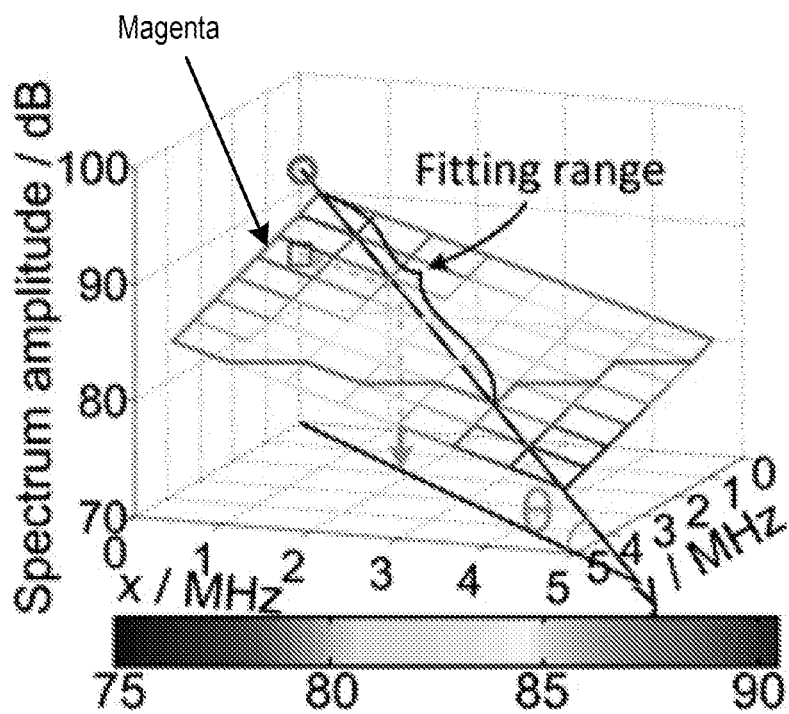

FIGS. 4(a)-4(b): illustrations of a 2D photoacoustic spectrum analysis (PASA) method. 4(a) Photoacoustic (PA) power spectrum of a fatty liver sample over the highest 20 dB range. 4(b) First order model fitted to (a) and the definition of PASA parameters. The magenta outlines in 4(a) and 4(b) indicate the range of the PA spectrum fitted to the linear model. "o" marks the intercept; "□" marks the midband-fit. The angle between the diagonal of the square containing the 2D linear model and the horizontal plane is defined as θ. The slope value is tan (θ).

Figure 5:
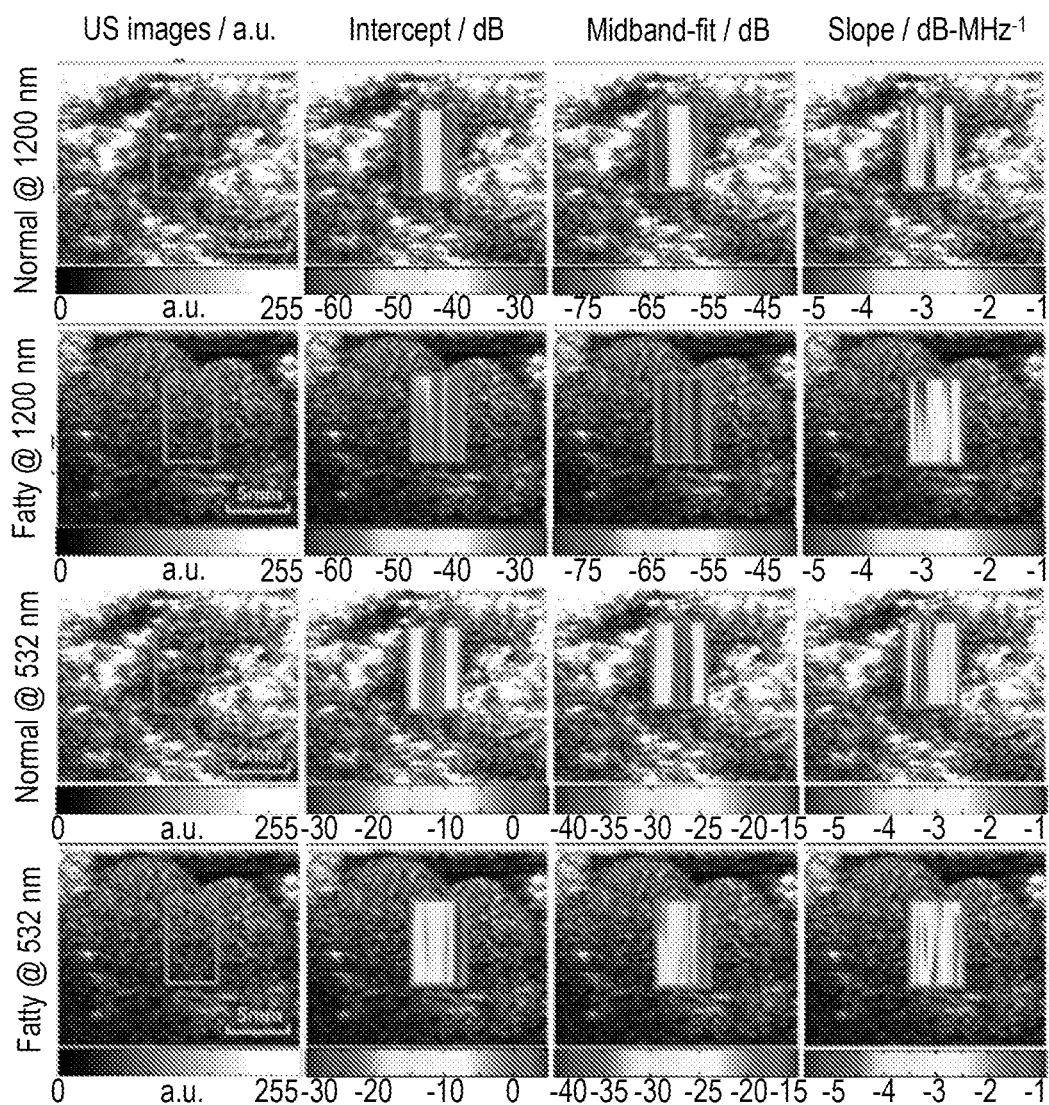

FIG. 5: shows images from in situ experiments at wavelengths of 1200 nm and 532 nm. Parameter distributions are calculated at each step of sliding window with Pwelch algorithm. Similar to those in ex vivo results, PASA parameters at a wavelength of 1200 nm, including an intercept, a midband fit, and a slope of normal tissue have lower values than those of fatty tissue. At a wavelength of 532 nm, normal liver shows higher intercept and midband-fit values, but lower slope values.

Figure 6:
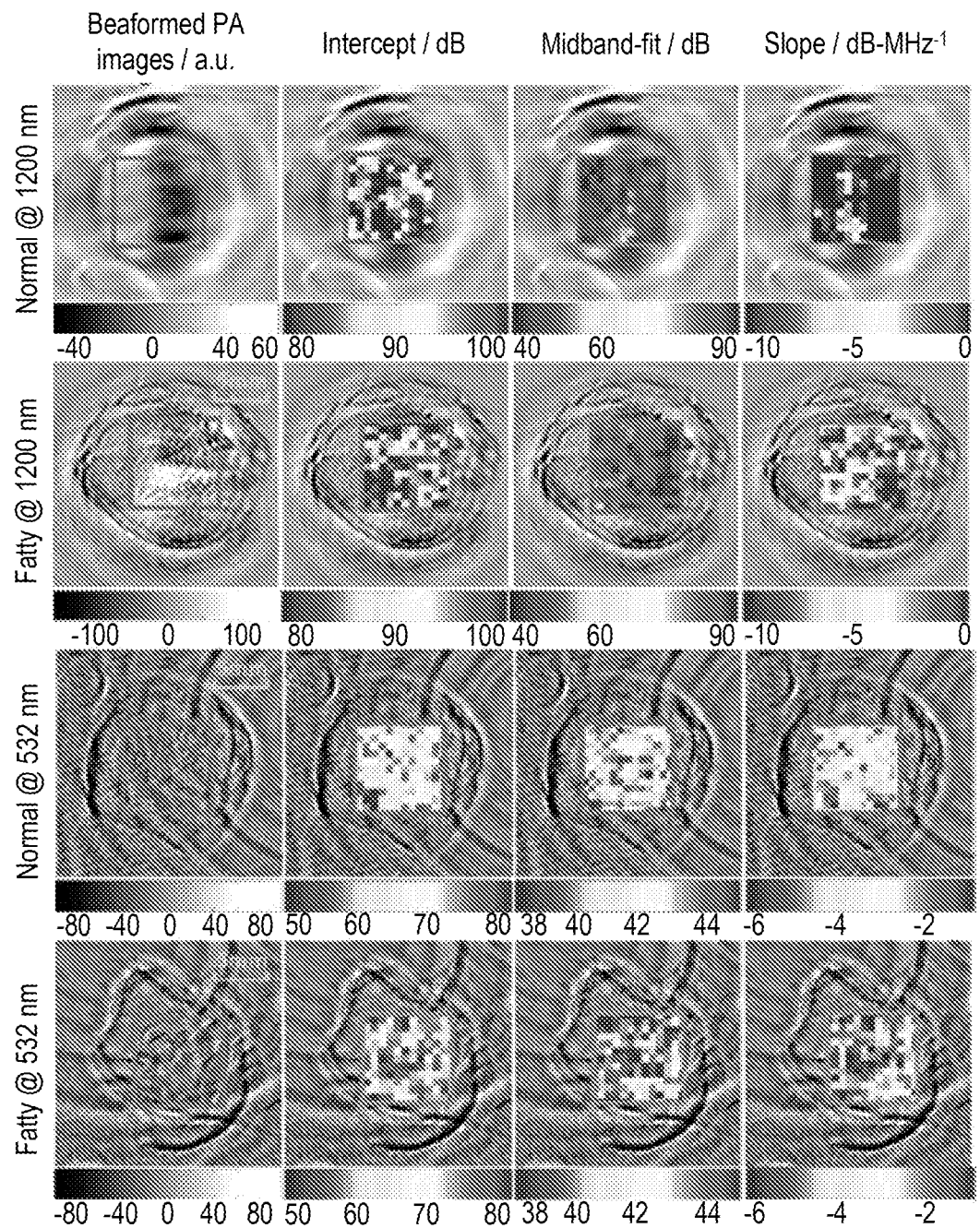

FIG. 6: shows pixel-wise PASA parameters of typical sample specimens at wavelengths of 1200 nm and 532 nm. Parameter distributions are calculated at each step of sliding window with a 2D Pwelch algorithm. At a wavelength of 1200 nm, tissue from a normal liver shows lower intercept, midband-fit, and slope values compared with tissue from a fatty liver. At a wavelength of 532 nm, compared to tissue from a fatty liver, tissue from a normal liver shows higher intercept and midband-fit values, but lower slope values.

Figure 7:
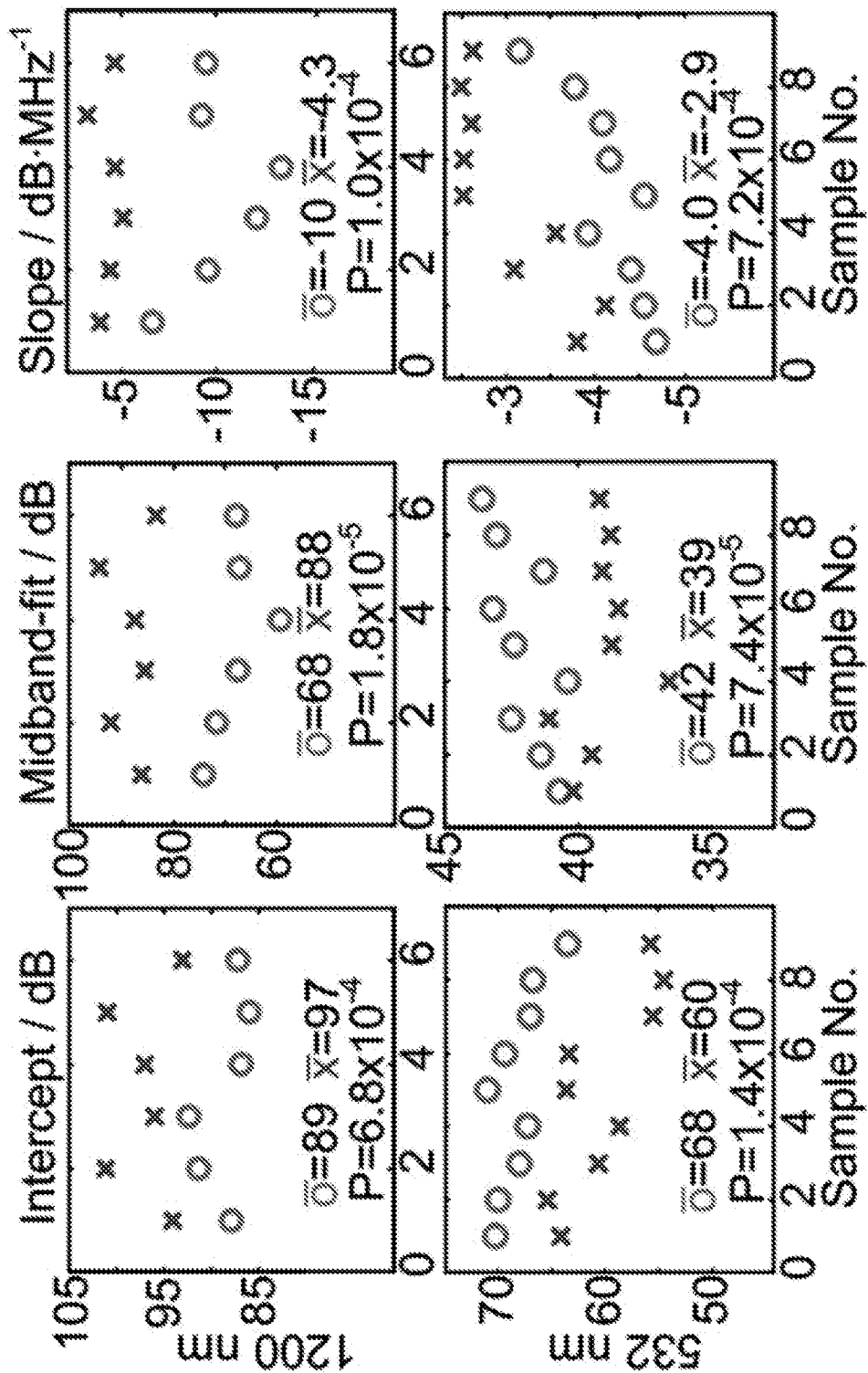

FIG. 7: shows statistical analysis of the PASA parameters from the ex vivo experiment at wavelengths of 1200 nm and 532 nm, respectively. "o" and "x" are data points from normal and fatty livers, respectively, and "ō" and "x̄" are averaged PASA parameters of normal and fatty livers, respectively. P values are calculated by using two-tailed Student t test.

FIGS. 8(a)-8(i): illustrations of the concept of PCS. In panels shown as 8(a)-8(c), the chemical component change in the livers induces the macroscopic color change. The changes of the liver conditions also involve the physical microstructural change in the livers, as shown in the Sirium Red stained histology images in 8(d)-8(f). In 8(d)-8(f), collagen is stained in red and marked by blue arrows. The steatosis regions are outlined in green in 8(e). Each fingerprint (strip feature) in 8(g)-8(i) correlates to one of the chemical components in the livers. The heterogeneous distribution of a chemical component increases the extension of the corresponding fingerprint. The concentration change of a chemical component corresponds to the magnitude change (expressed by the color depth in 8(g)-8(i)) of its fingerprint.

FIGS. 9(a)-(j): show exemplary PCS maps of 9(a) normal liver, 9(b) a liver with steatosis, and 9(c) a liver with fibrosis. The fingerprints of hemoglobin, lipid, collagen, and water are marked by the orange, green, blue, and black arrows respectively. 9(d) shows the overall optical absorption spectra of the normal and the fatty livers, which are produced by summing the pixels in the PCS maps in normal scale along the column. 9(e) shows the relative optical absorption spectra of major chemical components in liver tissue. The vertical dashed lines show the matching between the absorption peaks of the chemical components and the fingerprints in the PCS maps. FIGS. 9(f)-(j) are the same PCS as FIGS. 9(a)-(e), respectively, but with a higher signal to noise ratio.

FIGS. 10(a)-10(l): show histology images and PCS of the normal (10(a) and 10(d)), steatosis (10(b) and 10(e)), and fibrosis (10(c) and 10(f)) stages in a progressive NAFLD model. In 10(a)-10(c), "*" indicates blood vessels or bile ducts, "□" indicates lipid infiltrated hepatocytes, and arrows indicate collagen content. Fingerprints of hemoglobin, lipid, collagen, and water are marked. The histology images 10(g)-10(i) are the same as 10(a)-10(c), respectively, and the PCS maps 10(j)-10(l) are the same as 10(d)-10(f), respectively, but with a higher signal to noise ratio.

Figure 11B:
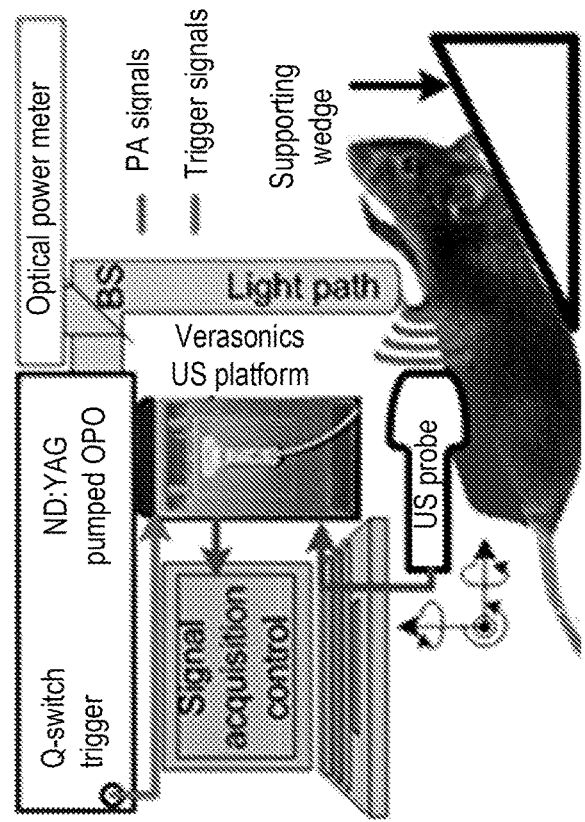
Figure 11A:
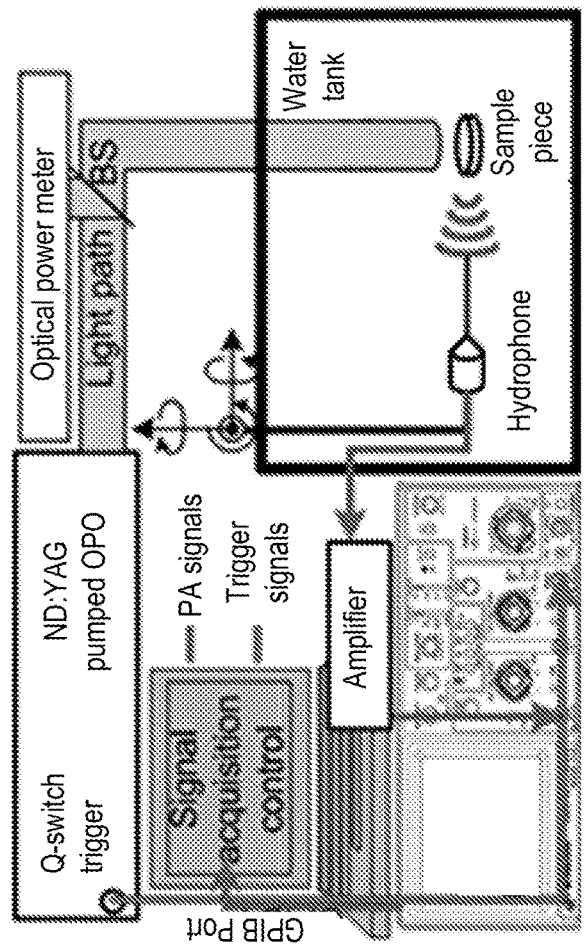

FIGS. 11(a)-11(b): show experimental setups for 11(a) ex vivo imaging and 11(b) non-invasive in vivo imaging of a mouse liver.

Figure 12:
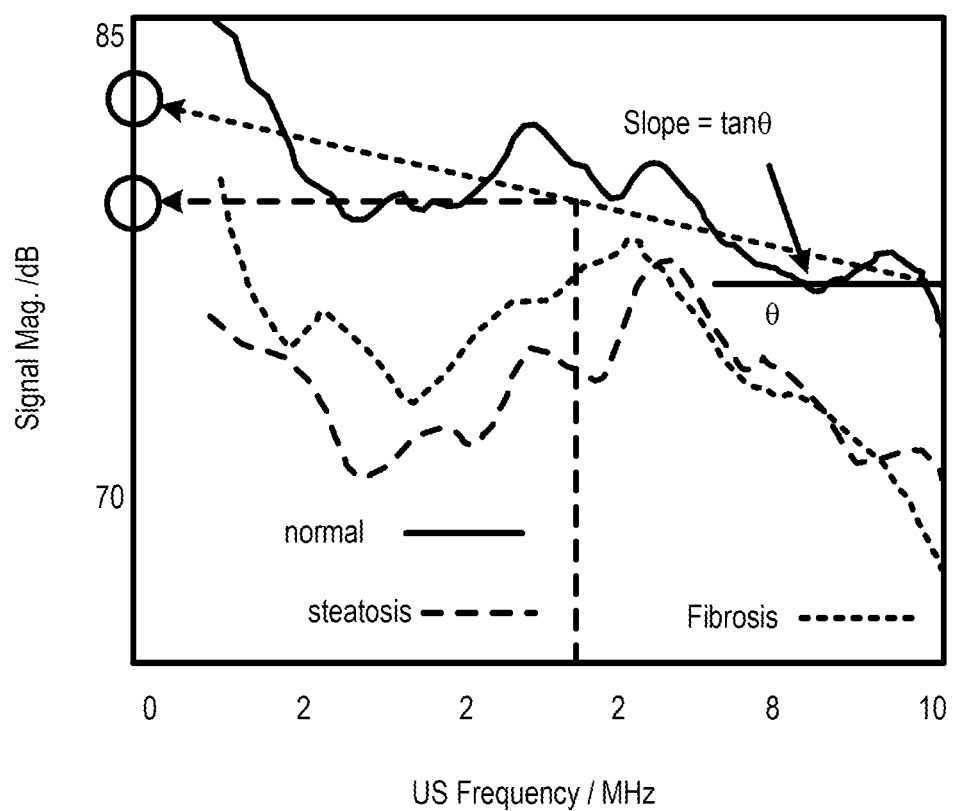

FIG. 12: shows a PA power spectra and corresponding linear-fit in 1-10 MHz of normal, steatosis, and fibrosis tissues at a wavelength of 700 nm. The arrow marks the high frequency components generated by the heterogeneous microstructure of the steatosis and fibrosis livers. The PASA parameters characterizing the linear-fit are illustrated on the result from a normal liver. The red circle shows the intercept, or the magnitude of the linear-fit at zero-frequency. The green circle shows the midband-fit, or the magnitude of the linear-fit at the center (5.5 MHz here) of the frequency range being analyzed. The arrow indicates that the slope value is the tangent of the angle between the linear-fit and the horizontal axis.

Figures 13A, 13B, 13C, 13D, 13E, 13F:
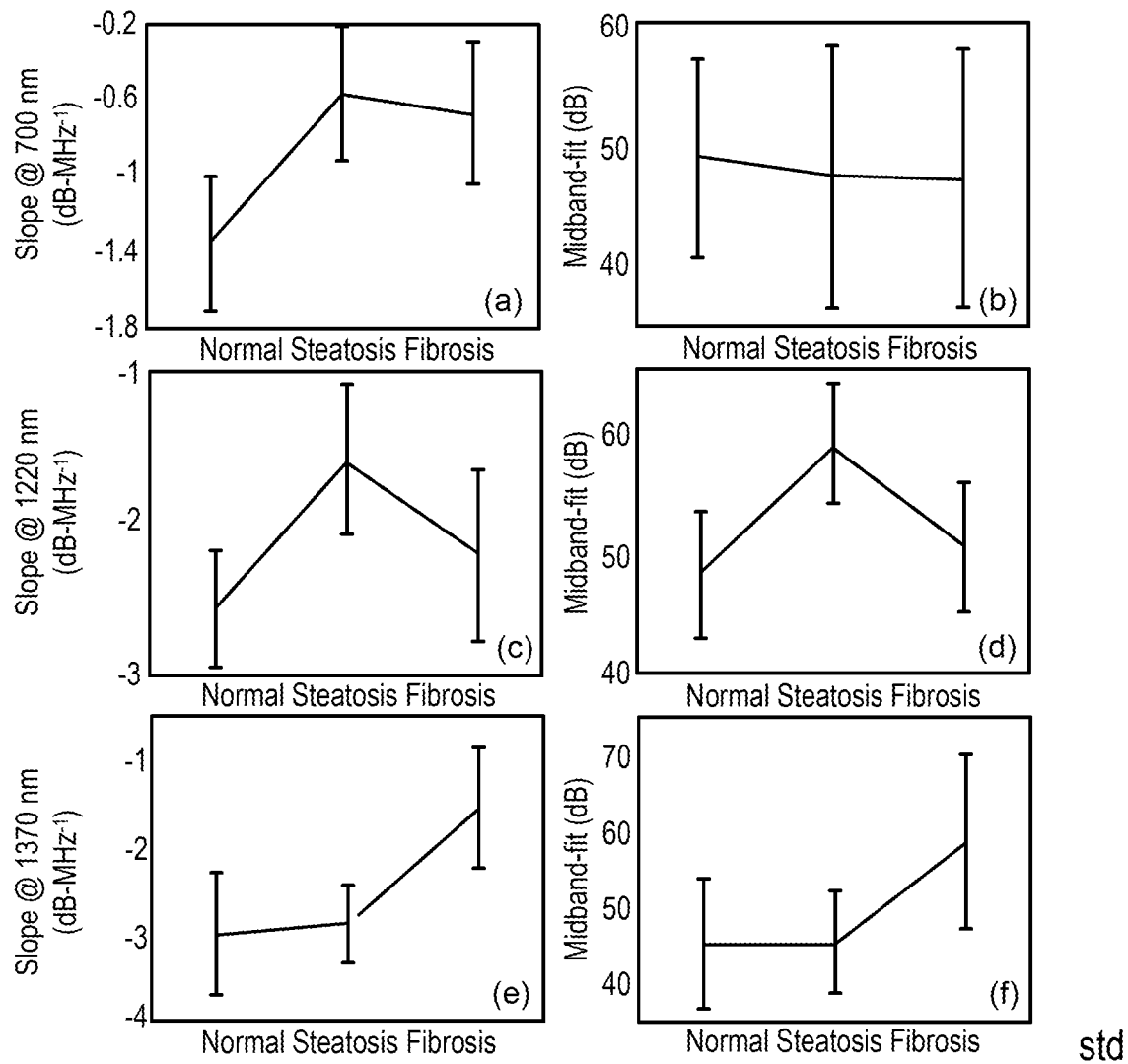
Figures 13G, 13H, 13I, 13J, 13K, 13L:
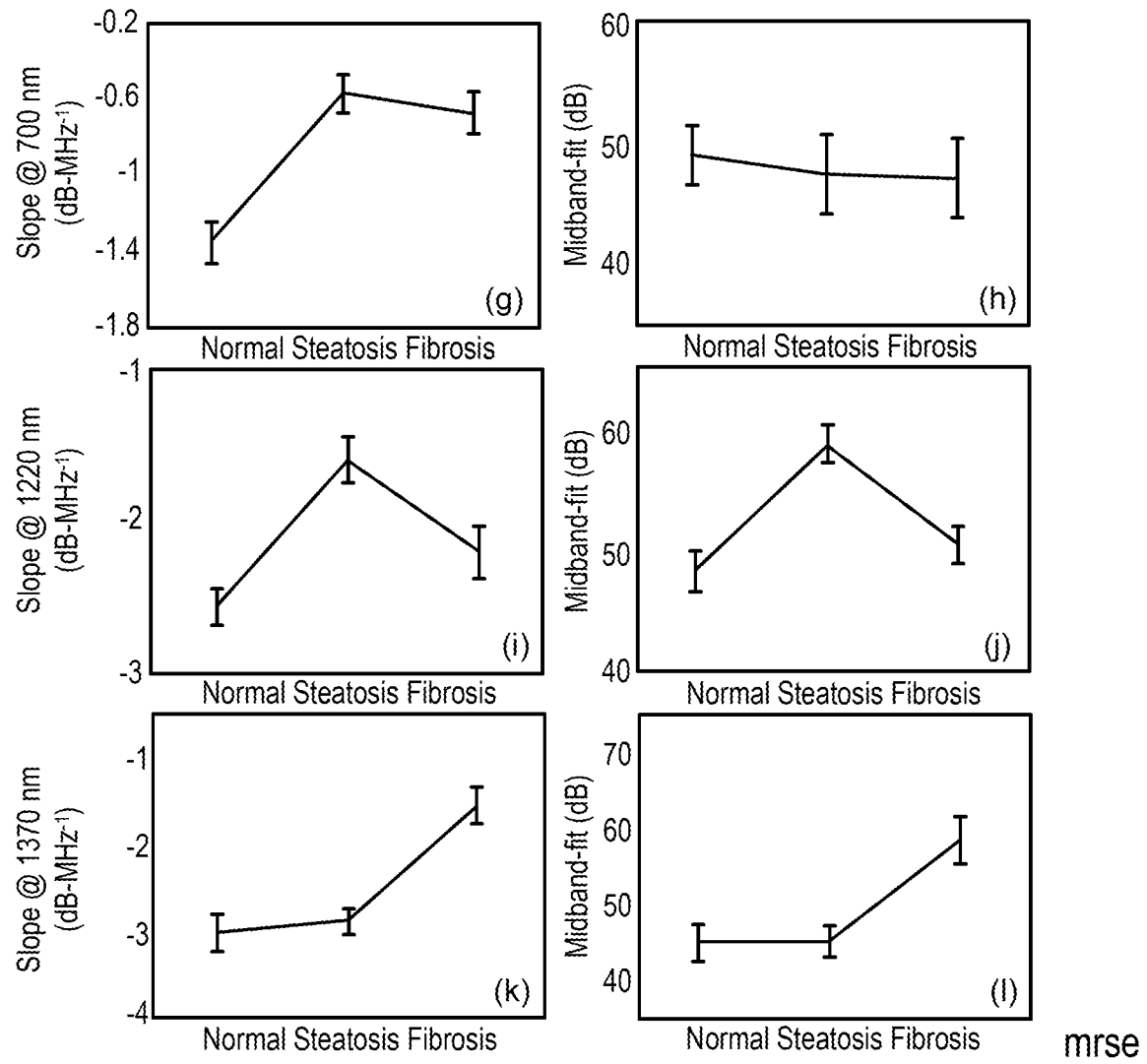
Figures 13M, 13N, 13O, 13P, 13Q, 13R:
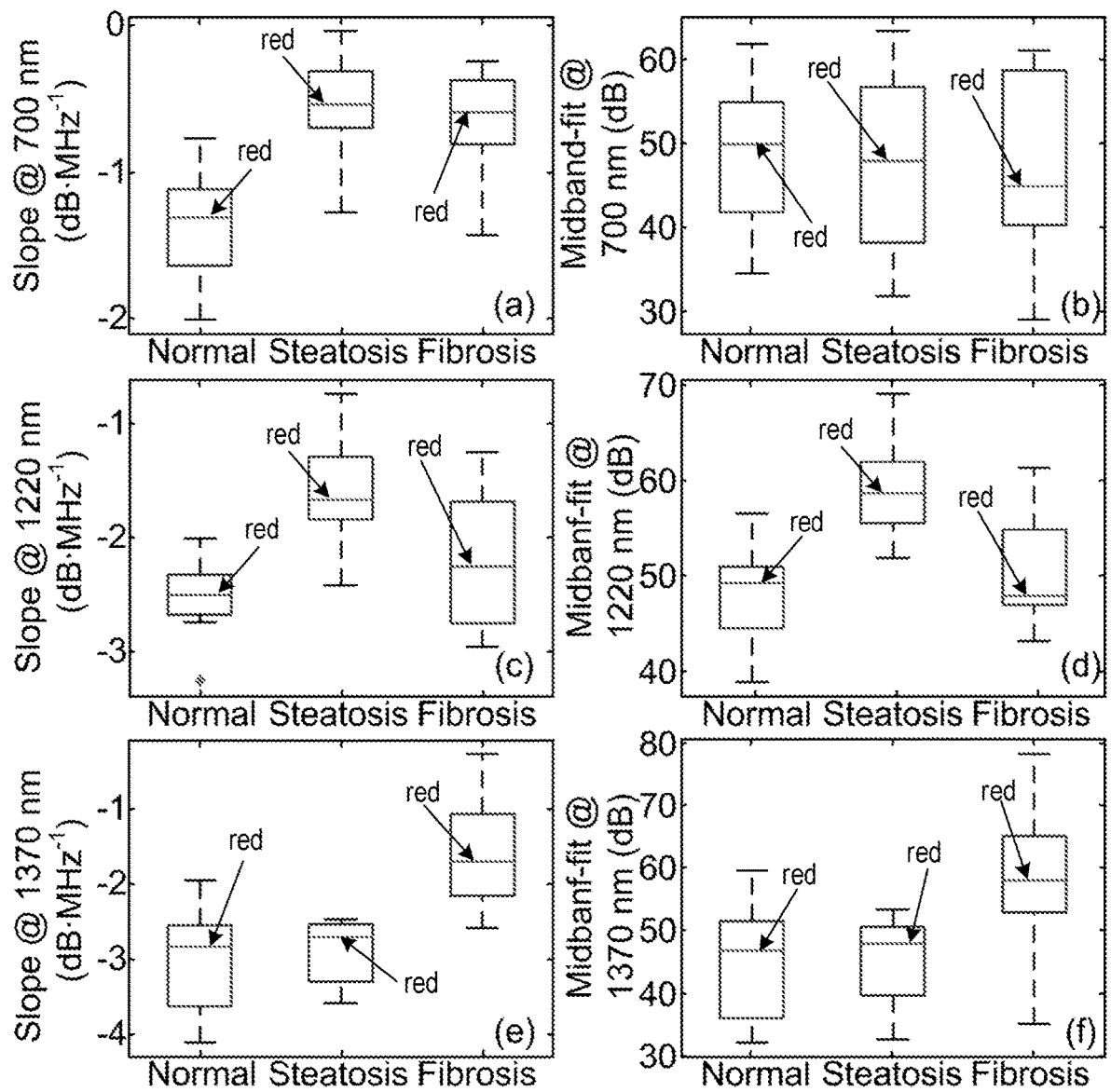

FIGS. 13(a)-13(r): show experimental data from progressive NAFLD mice. FIGS. 13(a)-13(l) show statistics of the experimental data from the progressive NAFLD mice. Each data group consists of 12 data points. Error bars indicate the mean values and the standard deviations (mean root square error) of the data. FIGS. 13(m)-(r) show the data groups as boxes with upper and lower edges. Red lines represent averages of the data points. The upper and lower edges are the $25^{th}$ and $75^{th}$ percentiles, respectively. The dashed lines extend to the most extreme data points and do not consider outliers. The outlier in (o) is plotted as "‡".

FIGS. 14(a)-14(b): show non-invasive, in situ imaging and PASA of murine liver tissue having various conditions, including a normal, healthy liver, a liver with steatosis, and a liver with fibrosis. 14(a) shows normal versus steatosis at a wavelength of 1220 nm. The steatosis liver shows higher PASA parameters than the normal liver. 14(b) shows normal versus fibrosis liver tissue at a wavelength of 1370 nm. The fibrosis liver shows higher PASA parameters than the normal liver.

FIG. 15: shows non-invasive, in situ imaging and PASA of mouse livers having a fibrosis condition and a normal healthy liver at a wavelength of 700 nm. Livers with fibrosis show lower intercept and midband-fit due to the loss of the hemoglobin, yet higher slope values than the normal liver due to the heterogeneous distribution of the hemoglobin.

Figure 16:
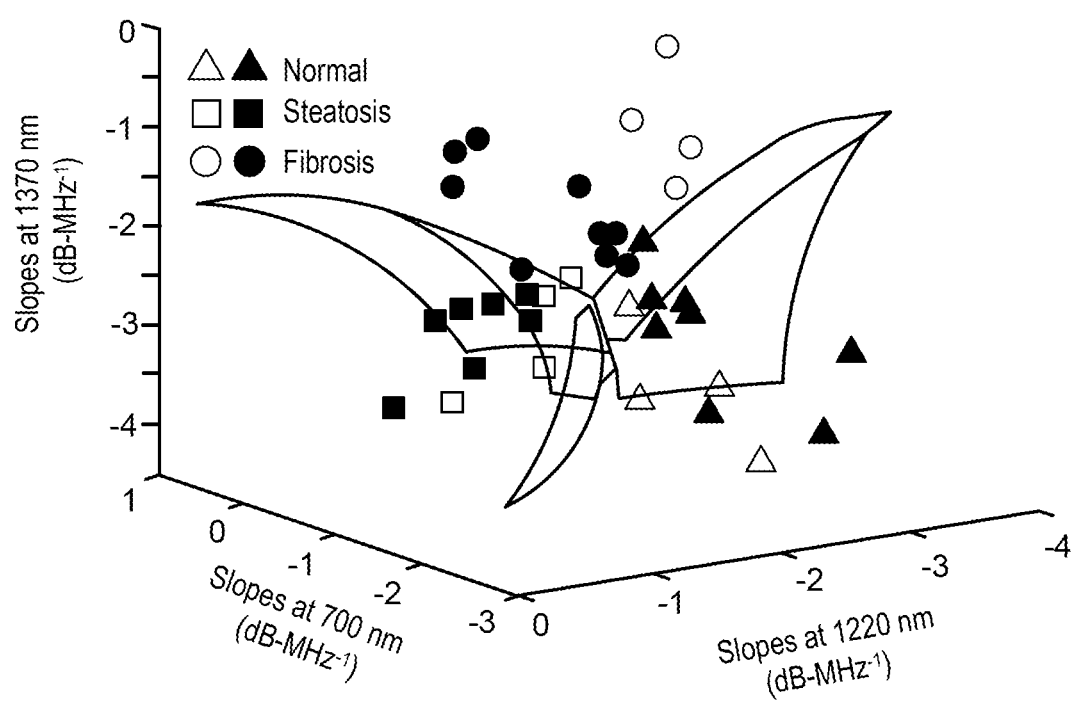

FIG. 16: shows a categorization of the slope values at wavelengths of 700 nm, 1220 nm, and 1370 nm in PASA by Support Vector Machine (SVM) for various liver conditions, including normal, steatosis, and fibrosis. "x" indicates the training sets and "o" indicates the data sets under diagnosis. The transparent curved planes are the decision planes for classification.

Figure 17:
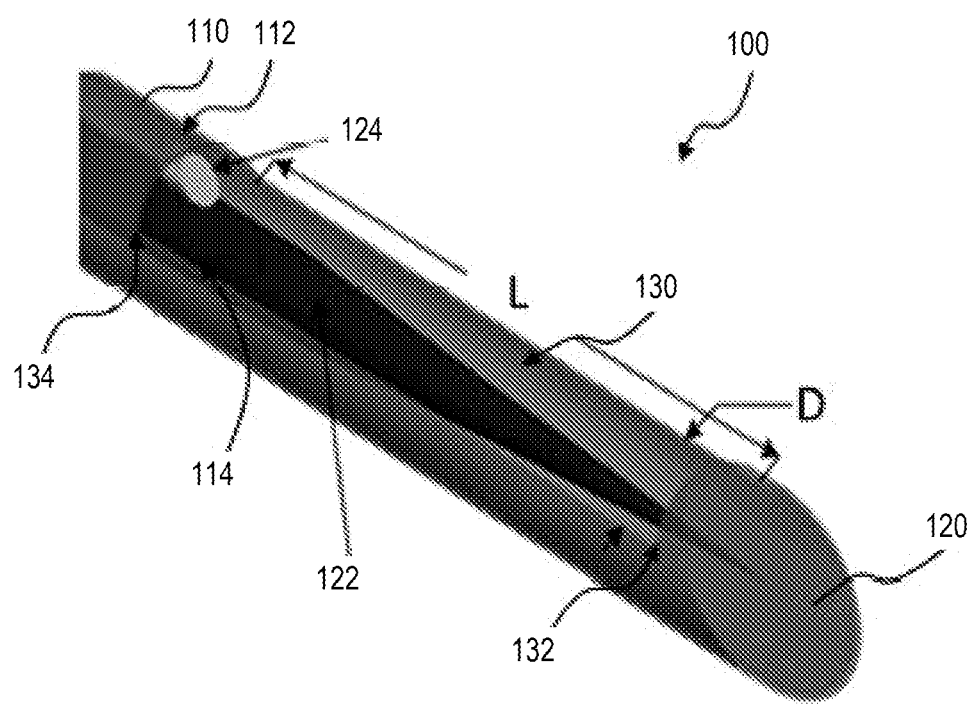

FIG. 17: shows a needle probe prepared in accordance with certain aspects of the present disclosure that that can be placed into or next to a target tissue for evaluation of regional conditions without performing a biopsy.

FIGS. 18(a)-(d): show results of a study of mouse livers performed with a probe according to the present technology. FIG. 18(a) is a photograph of a light illumination pattern provided by a side-firing fiber optic. FIG. 18(b) is a schematic illustration of a probe inserted into the mouse liver such that a fiber optic illuminates a location within the liver and a hydrophone detects the signal generated therefrom. FIG. 18(c) is a PASA of signals generated from a normal and fatty liver, respectively. FIG. 18(d) shows quantified slope values form 12 fatty liver specimens versus 12 normal controls.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The present technology provides a new approach to address certain diagnostic challenges. The present disclosure describes an entirely new diagnostic technology, photoacoustic physio-chemical analysis (PAPCA), which can facilitate objective assessment of both physical and chemical biomarkers of diseases in vivo, by way of non-limiting example. By performing photoacoustic scans of a tissue over a broad optical spectrum covering absorption fingerprints of specifically relevant chemical components in the tissue, and then transforming the signals into the frequency domain, a two dimensional (2D) physio-chemical spectrogram (PCS) can be generated, with one axis representing the optical spectrum and the other showing the ultrasonic frequency. Because the PCS can be done with a degree of spatial discrimination, each low resolution voxel will be a 2D spectrogram. The PCS, presenting the "optical signature" and the "ultrasound signature," simultaneously in one 2D map, contains very rich diagnostic information and can enable quantitative analysis of not only the concentrations but also the spatial distributions (or microstructures) of a variety of chemical components in the tissue. Non-limiting examples of the chemical components include hemoglobin, lipid, collagen, water, or any combinations thereof. The ultrasonic power spectrum at the optical absorption peak (e.g., the fingerprint) of each chemical component can be characterized by a first-order linear model. This characterization produces quantified spectral parameters associated directly with the concentration and the spatial distribution of this chemical component in the tissue. A complete set of spectral parameters form all specific chemical components to facilitate multi-variant discriminant function analysis, enabling objective categorization of different tissue types.

In certain aspects, methods of performing photoacoustic physio-chemical analysis (PAPCA) on a tissue are provided. The method comprises performing a plurality of photoacoustic scans on a tissue to generate a plurality of photoacoustic signals. Each photoacoustic scan can comprise a broad range of wavelengths. Thus, a photoacoustic scan can be conducted with electromagnetic radiation by illuminating the tissue to generate acoustic signals and detecting the acoustic signals generated from the tissue. In certain aspects, the electromagnetic radiation used for the photoacoustic scan has an optical wavelength or spectrum, meaning it may fall within ultraviolet light (UV) having wavelengths of about 100 nm to about 390 nm, visible light having wavelengths ranging from about 390 to about 750 nm and infrared radiation (IR) (including near infrared (NIR) ranging from about 0.75 to about 1.4 µm; short wave infrared (SWIR) ranging from about 1.4 to about 3 µm; mid wave infrared (MWIR) ranging from about 3 to about 8 µm; long wave infrared (LWIR) ranging from about 8 to about 15 µm; and far infrared (FIR) ranging from about 15 µm to 1 mm). The photoacoustic scans are performed by optically illuminating tissue in a subject with a source of electromagnetic radiation within a predetermined range of wavelengths. In certain variations, a preferred source of electromagnetic radiation is a laser and more particularly a pulsed laser. The photoacoustic scans can cover a single broad range of wavelengths (e.g., continuous, where the scan progresses through the range of wavelengths via stepped increments) or multiple ranges of wavelengths (e.g., discrete ranges of wavelengths). In certain embodiments, at least two distinct wavelength ranges are scanned. For example, in one embodiment, a first wavelength range is greater than or equal to about 680 nm to less than or equal to about 950 nm and a second wavelength range is greater than or equal to about 1200 nm to less than or equal to about 1700 nm.

The output of the pulsed laser is dependent on the optical energy density on a sample surface, but does not exceed a standard established by the American National Standards Institue (ANSI) for various anatomical features. However, in certain aspects, a signal-to-noise ratio corresponding to the photoacoustic imaging or measurement is sufficient, i.e., such that the signal is distinguishable from the noise. For example, the ANSI safety limit for human skin is 20 mJ/cm$^2$; therefore, the wavelength of the light is less than or equal to about 700 nm when skin is targeted by a pulsed laser, with the proviso that the signal-to-noise ratio is sufficient. In certain variations, and depending on the area (cm$^2$) of the anatomical feature being targeted, an energy output of the pulsed laser is greater than or equal to about 5 mJ per pulse to less than or equal to about 50 mJ per pulse. In certain other embodiments, the energy output of the pulsed laser is optionally greater than or equal to about 20 mJ per pulse to less than or equal to about 30 mJ per pulse. In certain preferred variations, the energy output of the pulsed laser may be greater than or equal to about 15 mJ per pulse to less than or equal to about 20 mJ per pulse. In certain aspects, a pulse duration of the pulsed laser can be greater than or equal to about 1 to less than or equal to about 50 ns, or greater than or equal to about 1 to less than or equal to about 25 ns, or greater than or equal to about 1 to less than or equal to about 10 ns. For example, in certain embodiments, the pulse duration can be about 1 ns, about 2 ns, about 3 ns, about 4 ns, about 5, ns, about 6 ns, about 7 ns, about 8 ns, about 9 ns, or about 10 ns. In certain preferred aspects, the pulsed laser pulse has a duration of about 8 ns. The scans may optionally comprise a tuning step size of greater than or equal to about 1 nm to less than or equal to about 50 nm. In certain aspects, a preferred tuning step size is about 10 nm. The laser beam may be collimated to a diameter of greater than or equal to about 0.25 inches to less than or equal to about 1.0 inch. In certain preferred aspects, the pulsed laser beam is collimated to about 0.5 inches in diameter. Preferably, the tissue is scanned a plurality of times at different regions or areas. For example, 1, 2, 3, 4, or 5 regions of a tissue can be scanned.

The tissue to be subjected to the present methods may be any tissue. In certain variations, the tissue is within a body of any animal or subject that is typically imaged by US or PAI. In various embodiments, the tissue is a section or region of an organ. Non-limiting examples of tissue include liver, breast, prostate, kidney, lung, nerve, thyroid, connective tissue, vascular tissue, and fat pad. The tissue can be from a mammal, bird, reptile, or amphibian, by way of non-limiting example. In preferred embodiments, the animal is a human or non-human mammal, such as a mouse, dog, or horse.

The method further comprises transforming the photoacoustic signal at each wavelength into a frequency domain to create a power spectrum. Consequently, transforming photoacoustic signals at each wavelength into frequency domains creates a plurality of power spectra. The method also comprises generating a two dimensional (2D) physiochemical spectrogram (PCS) from the power spectra. The PCS comprises a first axis representing an optical wavelength and a second axis representing ultrasonic frequency. In this regard, the PCS provides physical and chemical information about the tissue being subjected to evaluation, which can be used to determine a condition of the tissue, for example, to diagnosis diseases. By analyzing the PCS, various biological markers from a tissue can be ascertained. For example, if the tissue is a liver, the PCS can indicate a concentration or amount of lipid, hemoglobin, water, and/or collagen present within the tissue. For example, a strong signal at an optical wavelength of about 1250 nm indicates a presence of lipids, which is a marker of non-alcoholic fatty liver disease. A strong signal at an optical wavelength of about 1350 nm indicates a presence of collagen, which is a marker of liver fibrosis. In certain aspects, the ultrasonic frequency indicates the micron scale tissue features, such as whether tissue is homogeneous or heterogeneous. A relatively stronger high ultrasonic frequency indicates a more heterogeneous tissue. A strong high frequency component appearing in the PCS at 1250 nm indicates increased tissue heterogeneity as a result of the increased lipid clusters in the fatty liver. A strong high frequency component appearing in the PCS at 1350 nm indicates increased tissue heterogeneity as a result of the increased collagen in the fibrosis liver. Therefore, by indicating chemical and physical biomarkers simultaneously, the PCS can be analyzed, for example, by photoacoustic spectrum analysis (PASA), to diagnose and monitor various conditions and disease states. Moreover, such diagnostic and analytical techniques can be used for much earlier diagnosis than with conventional methods.

Photoacoustic Spectrum Analysis

Although the PCS of tissue contains rich diagnostic information, PASA provides a method of analyzing PCS in order to establish objective and quantitative measurements. PASA can be used to quantify physical information, e.g., density, dimension, periodic features, of micron-sized optical absorbers in tissue. Also, PASA can evaluate sub-resolution features and can assess high-frequency structures without using a high-frequency probe. PASA offers fundamental advantages for addressing a number of practical problems faced by PAI, such as, for example: (1) PASA separates the effects from system components and tissue properties on image features, and delivers system-independent quantitative results, (2) averaged power spectra provide a cogent means of addressing the stochastic nature of tissue microstructure, and lead to measurements that are quantitative and repeatable, and (3) capability of operating at relatively low frequencies avoids the high cost and limited imaging depth associated with high-frequency PAI systems.

PASA quantifies a RF PA signal by generating three spectral parameters of the linear fit to the signal power spectrum, including intercept, midband fit, and slope. These parameters are closely relevant to histological microfeatures of optically absorbing substances, such as, for example, lipid droplets or fiber collagen. Among the three parameters, slope is the quantitative expression of the extension of a fingerprint in the PCS (the longer extension the higher slope), while both intercept and midband fit are more relevant to the intensity of the fingerprint. As a non-limiting example, PASA can be used to differentiate various liver conditions, including normal, steatosis, and fibrosis.

To better differentiate different tissue conditions, including the liver conditions described above, instead of relying on a single spectral parameter, the entire PCS can be studied. For example, multi-variant discriminant function analysis can be performed by considering the spectral parameters at multiple fingerprints, or independent component analysis can be performed to capture the unique features of the 2D PCS.

To present the spatial distribution of histological microfeatures in a sample, 2D or 3D PASA can be performed to generate 2D or 3D spectral parameter images. Compared to intensity based PA 9 imaging of morphological structures, PA spectral parameter imaging at the optical fingerprints of relevant chemical substances, by presenting their histological microfeatures, renders higher contrast among different tissues and leads to improved diagnosis by offering better sensitivity and specificity.

A series of experiments are performed to investigate the use of PASA to identify microstructural changes corresponding to fat accumulation in mouse livers ex vivo and in situ. Specifically, prominent differences between PASA parameters from fatty and normal mouse livers are observed. The analysis of the PASA parameters from six normal and six fatty mouse livers indicates that there are differences of up to 5 standard deviations between the PASA parameters of the normal livers and those of the fatty livers at a wavelength of 1200 nm. The PASA parameters from nine normal and nine fatty mouse livers at a wavelength of 532 nm, the differences are approximately 2 standard deviations ($P<0.05$). The results support a hypothesis that the PASA allows quantitative identification of microstructural changes that differentiate normal from fatty livers. Compared with that at 532 nm, PASA at 1200 nm is more reliable for fatty liver diagnosis.

By way of background, biopsy has been widely used for evaluating, diagnosing, and monitoring many diseases, because it directly reveals histological changes in biologic tissues. However, the invasive nature and the length of time it takes to perform a biopsy make it a less desirable imaging option for many conditions. The diagnosis and treatment monitoring of many diseases can be drastically improved by using a non-invasive imaging modality that facilitates the quantification of histological microstructures with adequate sensitivity and specificity. In PAI, light from a pulsed laser is used to illuminate a biological sample. The light energy deposition in the tissue leads to an instant temperature rise and thermoelastic expansion, which induces ultrasonic waves (e.g., PA signals). Although they are very weak in intensity, PA signals can be collected by using US transducers or other US detectors for later reconstruction of an image of the sample. Compared with conventional optical imaging, the spatial resolution of PAI is not limited by strong light diffusion, but instead, is determined by detecting PA signals. Therefore, PA imaging has a major advantage over existing optical modalities and can render detailed features in optically scattering tissue, even when an imaging depth is beyond the optical mean free path. As an example, PAI of the human breast has been achieved recently with satisfactory special resolution at a depth of up to 5 cm from the skin surface.

Previously, PA imaging has been focused on exploring the intensities of the PA signal from biologic tissue as an indication of macroscopic optical absorbance. For example, frequency domain power distribution (power spectrum) of the broadband radiofrequency PA signals also encodes texture information in the regions of interest. Signal power spectrum analysis in US imaging has also been investigated. USSA has been used to study the intensity attenuation and frequency or phase shift of the backscattered US waves and periodicity captured by the spectrum and allows discrimination of microscopic features in biologic tissue. Similar to US spectrum analysis, PA spectrum analysis (PASA) allows evaluation of the intensity and, more importantly, the "pitch" or frequency of the PA signals.

Normal, healthy mouse livers possess compact cell structures and abundant red blood cells in the intercellular sinusoids, but no noticeable accumulation of fat, as shown in FIG. 1. When fat accumulates in experimental models of obesity, the number of red blood cells per unit area decreases. As shown in FIG. 2, the molecular vibrational absorption peak of the carbon-hydrogen bond in a lipid molecule at a wavelength of approximately 1200 nm and the hemoglobin absorption spectrum peak at a wavelength of approximately 532 nm enable studying the lipid and red blood cell distribution in liver tissue. Several hypotheses can be made based on the histological findings in FIG. 1: (a) higher spectral intercept and midband-fit values in a first-order model will be observed at 532 nm in normal liver tissue because of the higher blood content in normal livers compared to fatty livers; (b) higher spectral intercept and midband-fit values will be observed at 1200 nm in fatty liver tissue because of the increased lipid content in fatty livers compared to that of normal livers; and (c) negative slopes with smaller absolute values will be observed in fatty livers at both 1200 nm and 532 nm, because the heterogeneous tissue structure in fatty livers will generate high frequency components, whereas the more homogeneous normal livers primarily produce low-frequency PA signals at both 1200 nm and 532 nm.

As described herein, the capability of PASA to allow identification of the microstructure changes corresponding to fat accumulation in mouse livers is explored through ex vivo and in situ experiments.

Materials and Methods

The laboratory animal protocol for this work was approved by the university committee on use and care of animals of the University of Michigan.

Animal Model Preparation

C57BL/6J wild type mice (Jackson laboratory) were used in this study. An obese group was fed with chow diet for the first 8 weeks, followed by 60% fat diet (diet research, D12492) for 12 weeks thereafter. A control group was fed a chow diet for 20 weeks. Both groups were sacrificed at the end of the 20th week. The obese and the control groups each included 16 mice, with six and nine mice for ex vivo experiments at 1200 nm and 532 nm, respectively, and one mouse for an in situ experiment.

Experimental Setups

Comparable to that of radiofrequency US signals, the power spectrum of the radiofrequency PA signals in dB can be approximated by a first order model. Three parameters, including an intercept, a midband fit and a slope of the first order model, are extracted afterwards. An intercept is a magnitude of the linear model at zero frequency, representing the low-frequency components of the signal power spectrum. A midband fit is a magnitude of the linear model at the center frequency of the fitting range, representing an averaged signal spectrum magnitude in the entire fitting range. An intercept and midband fit both reflect the macroscopic absorption of the biologic tissue. A slope represents a distribution of the frequency components of the radiofrequency PA signals. Higher slope values indicates more high-frequency components and equivalently more heterogeneous tissue texture, whereas comparatively lower slope values indicate more homogeneous tissue features. In this study, to achieve desirable signal-to-noise ratio, PA signals were averaged 100 times in both the ex vivo and in situ experiments.

Ex Vivo Experiment.

A home-built setup for ex vivo PA imaging experiments is illustrated in FIG. 3. The optical illumination was generated by a tunable Optical Parametric Oscillator pulsed laser (Vibrant B, Opotek Inc., Carlsbad, Calif.) pumped by a second harmonic output of an Nd:YAG pulsed laser (Brilliant B, Quantel, Bozeman, Mont.). For imaging at a wavelength of 1200 nm, a laser beam with 18 mJ per pulse and pulse duration of 8 ns was collimated to 13 mm in diameter to a sample piece, achieving an averaged light fluence of 13.6 mJ/cm$^2$ on the sample surface (within the safety limit of the American National Standards Institute regulations). The sample piece was cut from an intact lobe of a mouse liver into a disc shape with a diameter of about 13 mm and a thickness of about 1-2 mm. For the experiment at 532 nm, the light beam used from the pumping laser is at an energy level of 200 mJ per pulse. After the beam was expanded to 50 mm in diameter, the average light fluence on the sample surface was 10.2 mJ/cm$^2$.

A needle hydrophone (HNC-1500, ONDA Co., Sunnyvale, Calif.), with a detection bandwidth of 20 MHz centered at 10 MHz with a frequency dependent response variation of ±3 dB was used to acquire PA (ultrasonic) signals. To perform 2-D tomographic imaging of an ex vivo liver, a circular scan of the needle hydrophone around the tissue with a scanning radius of 17.5 mm was conducted, as described in Xie et al, Ultrasound Med. Biol. 39(11) pp. 2176-2184 (2013) and Wang et al. Nat. Biotechnol. 21(7) pp. 803-806 (2013), both of which are expressly incorporated herein by reference in their entireties.

For ultrasonic coupling, both the hydrophone and the liver tissue were placed in a tank of water. The liver tissue was fixed in a cylindrical sample holder made from porcine gel. After amplification by a total of 60 dB by using a preamplifier (30 dB, AH-2010, ONDA) and a low-noise amplifier (30 dB 5072PR, Parametrics, Waltham, Mass.), the PA signal received by the hydrophone was recorded with a digital oscilloscope (TDS 540, Tektronix, Inc., Beaverton, Oreg.) at a sampling rate of 250 MHz. LabView control synchronized the laser firing, the data acquisition of the oscilloscope, and the rotation of the hydrophone. PA signals were acquired at 240 angular positions evenly distributed around the sample.

After down-sampling to 50 MHz, the PA signals were used to reconstruct an image of the sample with a modified back-projection algorithm. The power spectra of the regions of interest in the ex vivo experiment were calculated by the Pwelch method extended to 2D as follows:

1) the subsections of a region of interest are selected with an 80×80 pixel slide window (corresponding to 1.6 µs in this study), with 5-pixel step size in both directions;

2) damp the edges of the subsections with a 2D hamming window and calculate the 2-D Fourier transform $F(\omega)$ of each subsection from Formula (1):

$$F(\omega) = \int_{-\infty}^{\infty} \int_{-\infty}^{\infty} f(x,y) e^{-2\pi i x \omega} e^{-2\pi i y \omega} dx dy;$$

3) calculate the power spectrum of each subsection as $[F(\omega) \cdot F^*(\omega)]$;

4) sum the power distribution of all quadrants to the first following the symmetry of the spectrum; and 5) average the power spectra of all subsections as the power spectrum of the region of interest.

FIG. 4(a) shows the 2D power spectrum in the range of [0.3 MHz, 4.6 MHz] within the magenta box in column 1, row 2 in FIG. 6. Similar to a 1-D spectrum analysis method, the selected spectral region was characterized by a first-order linear model of Formula (II):

$$k_1 x_1 + k_2 x_2 + b = y$$

where $x_1$ and $x_2$ are the frequency axes of the 2D power spectrum; y is the magnitude of the spectrum in dB; $k_1$, $k_2$ and b are the unknown variables to be fitted to the power spectrum by least square method. Formula (II) represents a plane in the Cartesian coordinate system, as shown in FIG. 4(b), instead of a line in the 1D PASA. In addition, the power spectrum at each step of the sliding window in the Pwelch algorithm was also quantified by Formula (I), formulating the pixel-wise spectral parameter distributions in FIG. 6.

For the data acquired at 1200 nm, the spectral range of 0.3-4.6 MHz, corresponding to approximately the 20-dB level in the data bandwidth is assessed. The relatively narrow spectral range was selected to validate that PASA can allow evaluation of the microstructures in the tissue by using only part of the signal power spectrum. The frequency range started at 0.3 MHz because of the discretization of the frequency axes. Starting from 0.3 MHz instead of 0 MHz also partially excluded the low-frequency signal components produced by the light illumination on the background porcine gel. Before the data acquired at 532 nm is processed, the lowest 2 MHz spectral range is discarded to avoid the strong, low frequency PA signals generated form the light illumination on the background porcine gel. The power spectrum was analyzed in the wider range of 2-8.3 MHz of the 30-dB level.

In Situ Experiment.

In the in situ experiment, a customized US and PA dual-modality imaging system was used for rapid data acquisition, as shown in FIG. 3(B). This system is based on a US platform (Verasonics Inc., Redmond, Wash.) and a 128-element linear array (L7-4, Philips Healthcare, Andover, Mass.) working at a sampling frequency of 20 MHz. Powered by a graphics processing unit card that facilitates parallel computation, this system can perform PA and US imaging of the same object simultaneously at a frame rate of 10 Hz, which is limited by the pulse repetition rate of the laser. Because the laser used provides limited output energy of 18 mJ per pulse at 1200 nm, the abdominal cavity of the scanned mouse was opened by performing bilateral incisions to facilitate the exposure of the liver to avoid light attenuation in the belly, which reduces the signal-to-noise ratio. The laser beam with a diameter of 13 mm illuminated the liver surface with an average light fluence of 13.6 mJ/cm$^2$ for the scans at both wavelengths of 1200 nm and 532 nm. The alignment of the imaging plane to the liver tissue was first confirmed by US imaging. Q-switch of the laser triggered the US platform for PA signal acquisition. The signals collected by the US system were stored in the controlling computer for image reconstruction, display as well as later PASA. The pitch of 298 µm of the L7-4 probe was equivalent to the sampling frequency of approximately 0.19 MHz, assuming a 1560 µm/µs speed of sound. Because of the low sampling rate along the lateral direction compared to that along the axial direction, the in situ experimental data were processed with the one-dimensional PASA method described in Kumon et al, Ultrasound Med. Biol. 37(5) pp. 834-839 (2011), incorporated herein by reference. Each A-line of the beam formed RF signals within the regions of interest (approximately 4 mm×7 mm, as marked by the magenta boxes in FIG. 5) was analyzed by using the Pwelch method with a one-dimensional sliding window of 1.6 µs. The regions of interest were confirmed by a physician (with 9 years of experience in metabolism in cells, tissues, and organisms). The power spectra were afterward calibrated by the frequency response of the US probe following the method described in Kumon et al. The calibrated spectra were quantified in a range of 1.5-7.5 MHz of the 15-dB bandwidth of the probe. One normal and one obese mouse were examined at both 1200 nm and 532 nm. Each PASA parameter was averaged within the regions of interest.

Statistical Analysis

The intercept, midband-fit and slope values acquired from the ex vivo experiment at 1200 nm and 532 nm were examined by using a two-tailed student t-test. A P value of 0.05 was considered to indicate a significant difference. The statistical analysis was conducted with the built-in statistical functions in MATLAB™ R2011b (MathWorks, Natick, Mass.).

Results

Ex Vivo Experiment

The normal and fatty tissue types could be reliably identified at either wavelength with any of the three PASA parameters (FIGS. 6 and 7). There were differences of up to 5 standard deviations (i.e., the slope) between the PASA parameters from the fatty and the normal livers when they were imaged at 1200 nm. These differences were approximately 2 standard deviations (i.e., the midband fit and the slope) when the livers were imaged at 532 nm.

In Situ Experiment

The comparison between the PASA parameters from the normal and the fatty livers in situ in FIG. 5 and the Table 1 validated the hypothesis that at 1200 nm, the fatty liver possessed higher spectral parameters including slope, intercept, and midband fit, than did normal livers. At 532 nm, the fatty liver had high slope values yet lower intercept and midband-fit values compared with those of the normal liver.

TABLE 1

Average PASA Parameters the Regions of Interest in the in situ Model

| Parameter | 1200 nm | | 532 nm | |
| --- | --- | --- | --- | --- |
| | Normal | Fatty | Normal | Fatty |
| Intercept (dB) | 52.9 | −32.0 | 6.5 | −17.2 |
| Midband fit (dB) | −69.6 | −42.4 | −23.4 | −32.4 |
| Slope (dB · MHz$^{-1}$) | −2.3 | −3.7 | −3.3 | −3.7 |

US and PA spectrum analyses have similar procedures, yet the two methods are somewhat different. US spectrum analysis characterizes biologic tissue with narrow-band US waves backscattered due to the acoustic impedance mismatch, whereas PASA quantifies tissue microstructures by accessing the optical absorption contrast and by analyzing the broadband PA signals originated within the regions of interest. The reconstructed PA images based on the back-projection algorithm are fundamentally the 2D beam-formed wideband radiofrequency PA signals. The 2D spectrum analysis approach is introduced to evaluate the microstructures in the 2D scanning plane. In the 2D PASA described above, the sliding window for calculating the 2D power spectrum of each subsection of the PA image is square, and the sampling rates in the orthogonal dimensions are comparable to facilitate the slope calculation. Otherwise, the PASA would be reduced to one dimension along the dimension with the higher sampling rate to be similar to that for the in situ experiment. The square sliding window in 2D PASA also conforms to the presumption that the tissue texture is isotropic and ensures that the tissue texture is evaluated equally in both dimensions. In this experiment, the quantification of the optical absorption of the tissue represented by the intercept and the midband fit is still relative due to the lack of knowledge on the accurate light energy deposition. The quantitative comparability of these two PASA parameters relies on the uniform light fluence in the paired imaging experiment on fatty and normal livers. In comparison with the intercept and the midband-fit, the slope is least dependent on the light fluence and thus has vast potential to quantify the microstructures in the tissue.

The PASA that was focused on the total hemoglobin content in the liver was performed at a wavelength of 532 nm, benefiting from the very stable energy output and the high beam quality of the pumping laser working at 532 nm. Without being bound by theory, the increased overlapping of the normal and fatty livers at 532 nm compared with that at 1200 nm may have been because blood cells with an optical absorption peak at 532 nm exist in the sinusoids of both normal and fatty livers, whereas the lipid droplets exist only in fatty livers. Thus, for noninvasive imaging of the liver in vivo, the laser light in the near-infrared spectral region between 700 nm and 900 nm may be a better option because better imaging depth can be achieved in this optical window. Moreover, when multiple laser wavelengths corresponding to the optical absorption peaks of oxygenated and deoxygenated hemoglobin can be used, PASA may be helpful in evaluating the spatial distributions of these two major forms of hemoglobin in biologic tissues.

All the fatty livers were from extremely obese mice. However, it is believed that the sensitivity of PASA permits evaluation along the progression of steatosis. Thus, at earlier stages, multivariate analysis including all three or any two of the spectral parameters could work better when a single PASA parameter does not suffice for the identification of fatty livers. More advanced stages of fatty liver disease such as fibrosis, can also be characterized by using PASA, for example, at the optical fingerprint of collagen around a wavelength of about 1350 nm, because fibrosis is typically associated with elevated collagen content.

Limits on PASA could be related to the signal bandwidth of the scanning system and the penetration depth of the laser energy. Studies on human breast, which is rich in adipose tissue, demonstrate that the PA imaging depth reached 5 cm when the laser light is in the near-infrared spectrum region. This imaging depth is sufficient for the study of small animals including rats and mice and may allow for scanning of patients when the liver is imaged from the side to avoid the thick subcutaneous fat at the front of the abdomen. In the in situ experiment described here, because the laser was not sufficiently powerful, any attenuation of light before it reached the liver was avoided by opening the abdominal cavity. However, it is contemplated that a more powerful laser can also be used, so that no surgery would be necessary for small animals and the whole procedure could be conducted in a noninvasive manner.

The feasibility of differentiating fatty and normal livers by using PASA is also investigated. The ex vivo and the in situ experiments in a mouse model at both 1200 nm and 532 nm wavelengths validated hypotheses on the relationship between the spectral parameters and the microstructures in mouse livers, although 1200 nm illumination appears to be more promising for fatty liver identification. Therefore, in accordance with various aspects of the present disclosure, PASA may be used as an in vivo and noninvasive method to identify the microstructures in liver tissue to aid liver disease diagnosis.

Photoacoustic Physio-Chemical Analysis

A pathologic diagnosis of a disease requires information regarding both microstructural and chemical changes in tissue. However, most concurrent mono-physics imaging technologies register either chemical components or physical microstructures in biologic tissue. Taking advantage of the multi-physics nature of photoacoustic (PA) effect, a physio-chemical spectrum (PCS), which, in accordance with various aspects of the present disclosure for the first time, integrates microscopic morphology and chemical components of a tissue. The PCS contains rich diagnostic information that is comparable to that observed in pathology. Taking the identification of steatosis and fibrosis in liver for instance, the procedures of PA physio-chemical analysis (PAPCA) including the characterization and the classification of tissues types are used. Ex vivo and non-invasive in situ experiments with mouse models demonstrate that PAPCA can be used in non-invasive, in vivo examination of pathological changes in biologic tissue.

Spectroscopic optical imaging (SOI) provides an approach for identifying chemical components by their intrinsic absorption spectra. Observing a specific chemical component at its optical absorption peak wavelengths effectively suppresses other chemical components in biologic tissue. Nonetheless, strong light scattering in deep tissue undermines the possibility of recovering microscopic information with pure optical imaging.

As discussed above, photoacoustic (PA) imaging technology initiates an imaging process from an illumination of biologic tissue with a pulsed laser. The light energy deposited within the tissue volume leads to a thermoelastic expansion, which generates US waves as PA signals. The PA signals can be captured by traditional US transducers or imaging systems. The imaging modality inherits the merits of both the functional sensitivity of optical imaging and the spatial resolution of US imaging. Similar to SOI, the majority of previous studies on PA imaging are focused on the total signal magnitudes as representations of concentrations of specific chemical components.

The present disclosure contemplates use of a novel technology, PA physio-chemical analysis (PAPCA) for non-invasive evaluation of pathological changes in biologic tissue. By utilizing the multi-physics nature of PA imaging, a physio-chemical spectrum (PCS), which integrates a power spectra of RF PA signals along a full optical spectrum, is first formulated. Rich diagnostic information comparable to that in pathology, including that of chemical components within a tissue along optical wavelengths and the corresponding physical microstructures along US frequencies, will be extracted for evaluating liver conditions. The method is examined by differentiating liver steatosis and fibrosis in a clinical environment, which is a challenging problem. Ex vivo and non-invasively in situ experiments are conducted on mice with extreme liver steatosis and fibrosis. In addition, PCS of mouse livers with progressive non-alcoholic fatty liver disease (NAFLD) conditions, including steatosis and fibrosis, are characterized by multivariate analysis methods for diagnosis of liver conditions.

Methods

Mouse Models

Figures 9A, 9B, 9C, 9D, 9E:
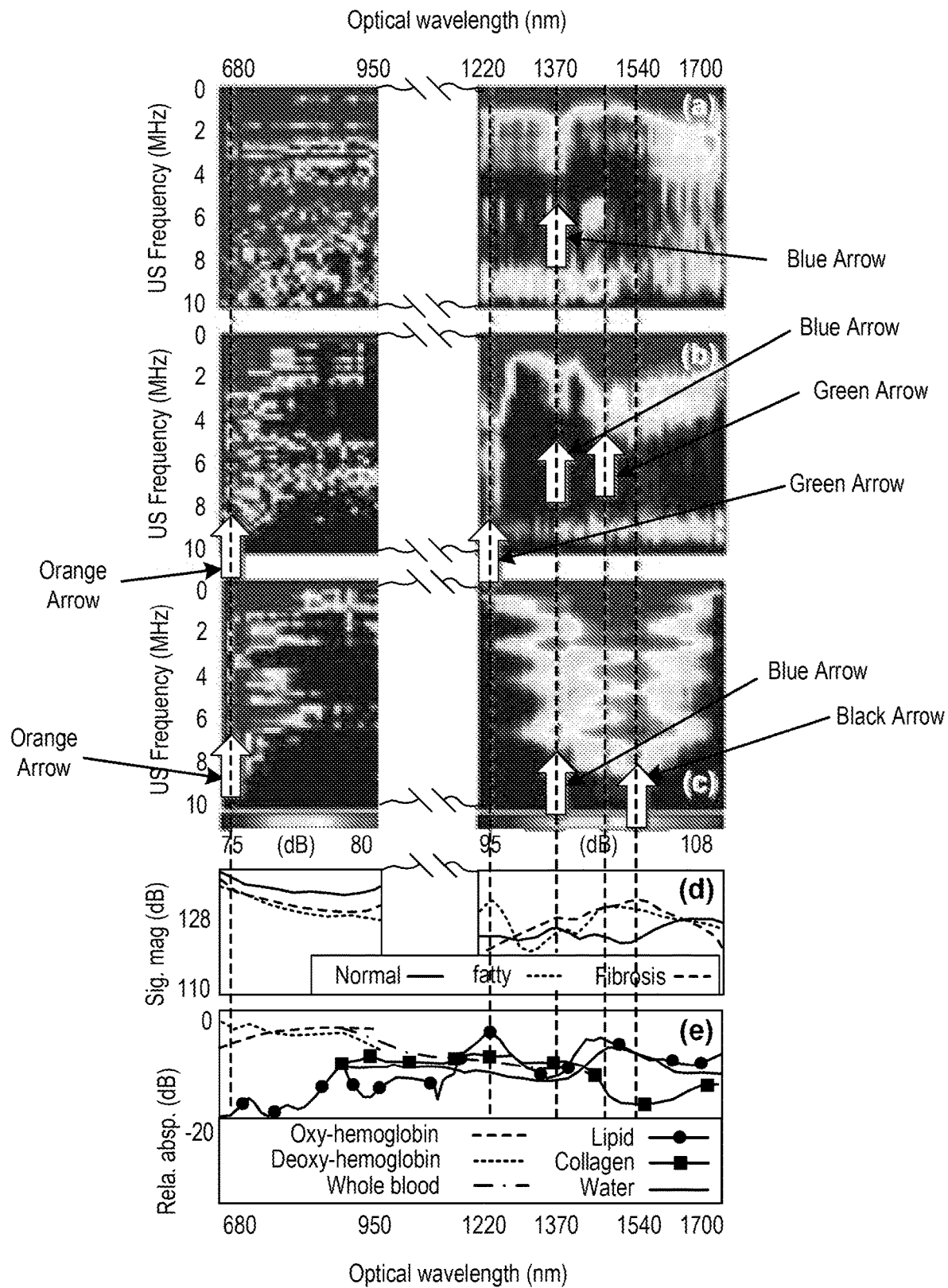

A steatosis liver used for acquiring the PCS in FIG. 9(b)(g) was generated in C57BL/6J wild type mice from Jackson laboratory. An obese mouse was fed a chow diet for 8 weeks, followed by a 60% fat diet (Research diet, D12492) for 12 weeks thereafter. A control mouse was fed a chow diet for 20 weeks. Both were sacrificed at the end of the 20th week.

A fibrosis model used for the PCS spectrum in FIG. 9(c)(h) was a FIP200 liver knock out (LKO) mouse, which spontaneously develops fibrosis. The mouse was fed a chow diet for 15 weeks. As shown in the histology images in FIG. 8(f), extreme fibrosis, but no steatosis, had occurred.

Figures 10A, 10B, 10C, 10D, 10E, 10F:
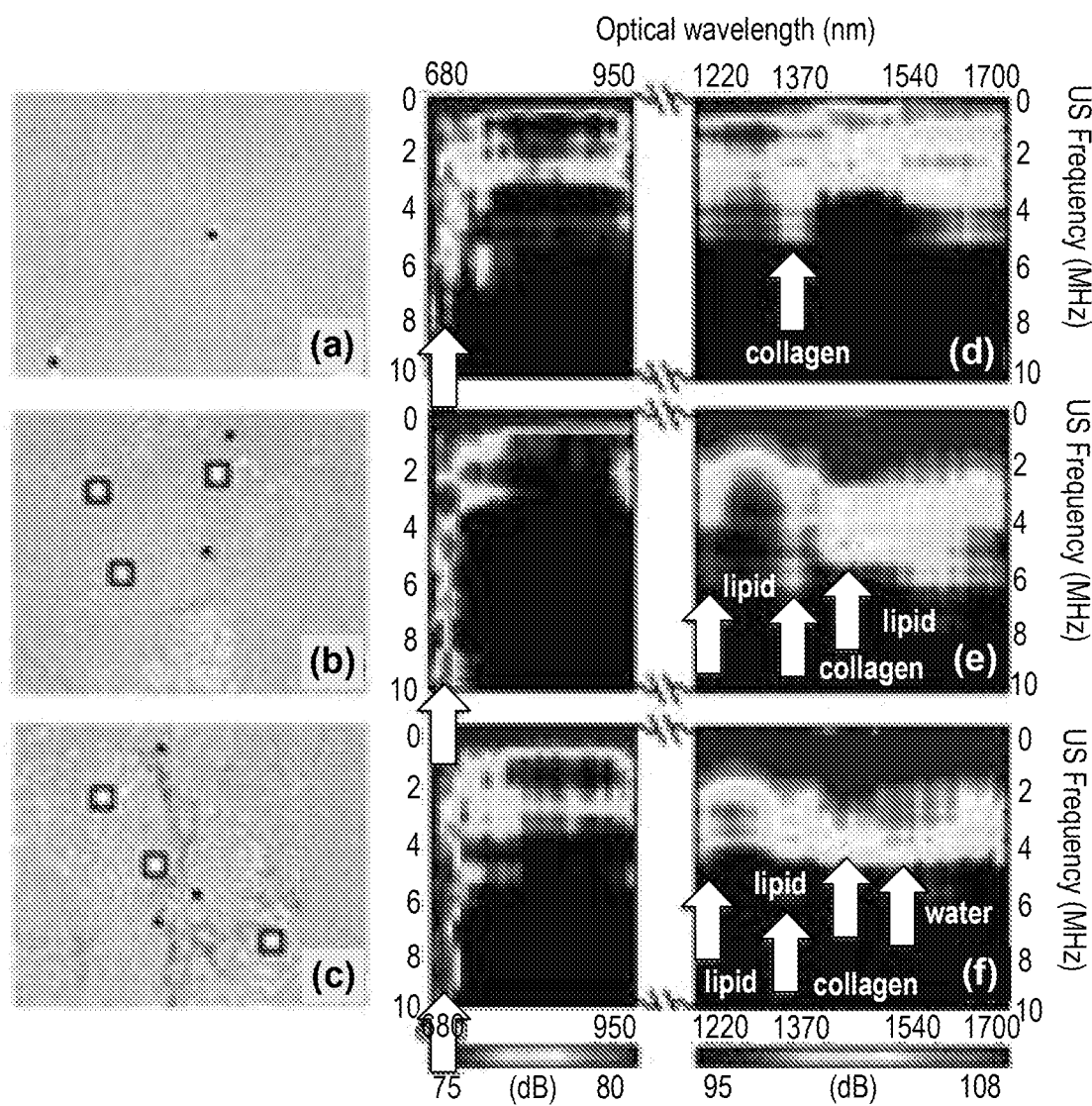
Figures 10G, 10H, 10I, 10J, 10K, 10L:
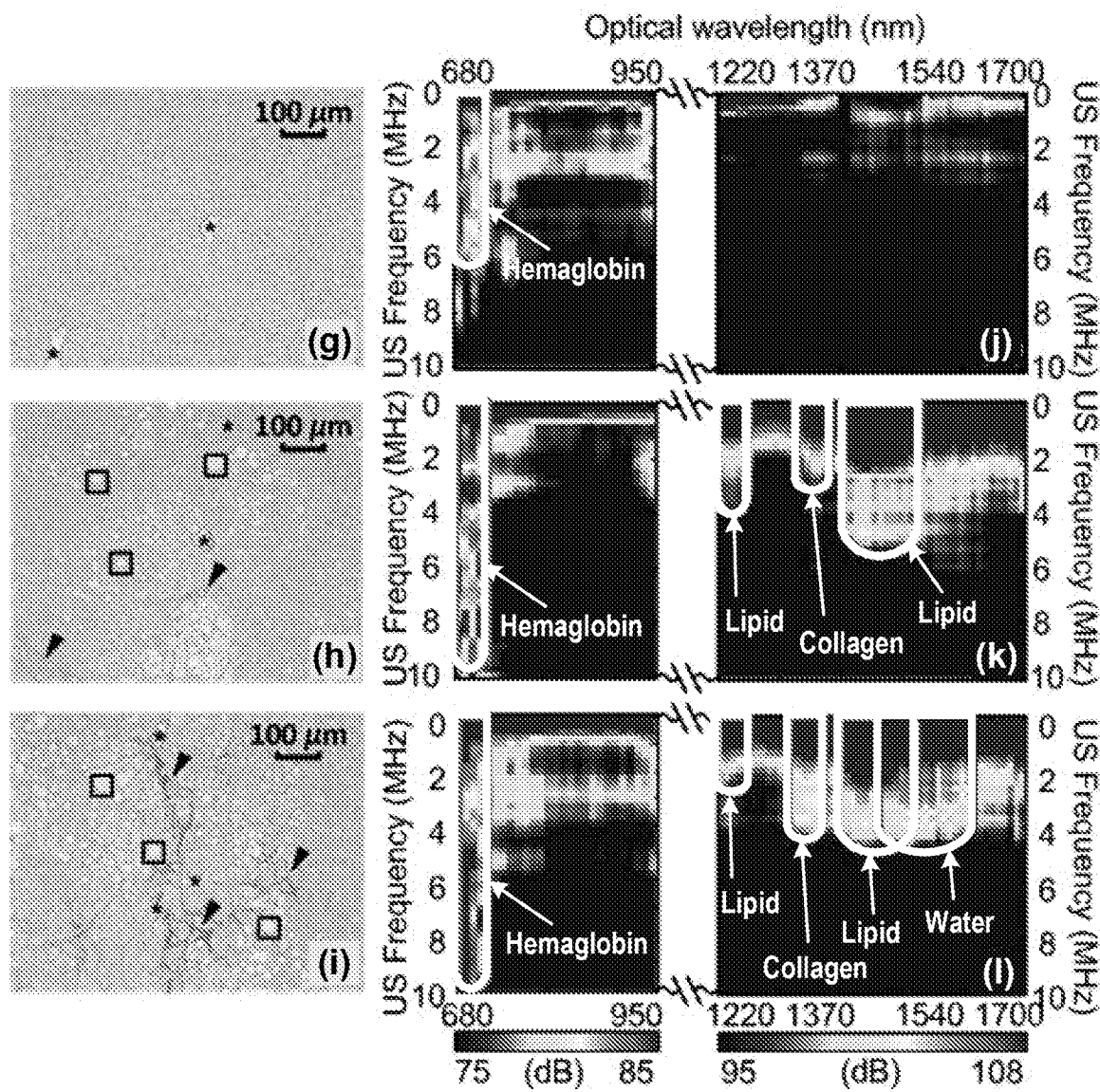

For a categorization study, a mouse model that quickly develops progressive NAFLD in liver (STAM, Stelic Institute & Co, Tokyo, Japan) is used. As confirmed by the histological images in FIGS. 10(b), 10(h), and 10(c), 10(i), the mouse livers developed steatosis at week 6 and fibrosis at week 12, although the steatosis and fibrosis level were not as high as those in FIGS. 8(e) and 8(f). For reference, histological images of normal rat livers are shown in FIGS. 10(a) and 10(g). A total of 9 mouse livers, 3 normal livers, 3 with steatosis, and 3 with fibrosis, were examined in ex vivo experiments. Each liver sample was scanned 4 times, covering different areas of the liver.

PCS Scanning System

A system for acquiring PCS from ex vivo tissues is shown in FIG. 11(a). Optical illumination in the system was generated by a tunable Optical Parametric Oscillator (OPO) laser (Vibrant B, Opotek Inc, Carlsbad, Calif.) pumped by a second harmonic output of an Nd:YAG pulsed laser (Brilliant B, Quantel, Bozeman, Mont.) with spectral linewidth of 15-20 cm$^{-1}$. The tuning ranges of the laser were 680-950 nm and 1200-1700 nm, covering a strong absorption range of hemoglobin in near-infrared (NIR) and vibrational absorption peaks of lipid, collagen, and water. A constant tuning step size of 10 nm was set during PCS acquisition. An energy output in both wavelength ranges was tuned to 15-20 mJ per pulse, with pulse durations of 8 ns. The laser beam was collimated to a half-inch in diameter. 10% of the laser energy was projected to an optical power meter by a beam splitter for energy monitoring and later signal magnitude calibration. The laser energy was below the American National Standards Institute safety level of 20 mJ/cm$^2$ in all experiments in this study. For ex vivo studies, the received PA signals were collected by a needle hydrophone (HNC-1500, ONDA Co., Sunnyvale, Calif.) with a broad receiving bandwidth of 0-20 MHz, so that the best frequency range for PASA of various liver conditions was determined. The signals received by the hydrophone were amplified and then digitized by a digital oscilloscope (TDS 540, Tektronix, Inc., Beaverton, Oreg.) before being collected by a PC.

The light source in the in situ experiments was identical to that used in the ex vivo setup. The data acquisition was conducted with a parallel PA-US, real-time imaging system shown in FIG. 11(b). A commercial US transducer array (L7-4, Philips, Andover, Mass.) covering a frequency band of 2.5-8.5 MHz was employed.

PCS Formulation and PASA

PA signals from tissue generated at each wavelength, after being transformed into a frequency domain, were calibrated by removing a system impulse response. A complete set of power spectra from all the optical wavelengths formed a PCS map, as shown in FIGS. 9 (a)-9(c), and 9(f)-9(h), with the intensities of the power spectra shown in pseudo-color. Because the signal-to-noise ratio of the hydrophone was less than that beyond 10 MHz, only frequency spectra between 0 and 10 MHz is presented in the PCS.

The PA signal power spectra corresponding to lipid and collagen were analyzed by the PASA methods described in Xu et al., Appl. Phys. Lett. 101(22) pp. 221102-221105 (2012), incorporated herein by reference. As illustrated in FIG. 12, the power spectrum derived from normal liver tissue was first fit to a linear model. The intercept, midband-fit, and slope values of the linear model were afterwards extracted for quantification of the magnitude (intercept and midband-fit) and frequency component distribution (slope) of the power spectrum.

Statistical Study and Categorization with SVM

As mentioned above, each of the 9 mouse livers were scanned 4 times and each scan covers a different region of the liver. A total of 36 PCS were generated, upon each of which PASA extracted the slopes and midband-fit values at 3 wavelengths; 700 nm, 1220 nm, and 1370 nm. Mean and standard deviation (or mean root square error) values of the slopes and midband-fits of mouse livers with the same conditions were calculated by the built-in functions in MATLAB™ (2011b, Mathworks, Boston, Mass.) and shown in FIGS. 13(a)-13(r). A MATLAB code library, LIBSVM was used for classifying liver conditions and examining the feasibility of implementing PAPCA for a diagnosis of liver conditions. The PASA parameters are used from two of the three liver samples in each category (normal, steatosis and fibrosis) for training the SVM (24 data sets=(3 categories×2 livers×4 scanned regions) and the rest (12 data sets=(3 categories×1 livers×4 scanned regions)) for examining diagnosis accuracy. A C support-type SVM is used with radial basis kernel in which the regularization parameter was set as 10 and the exponential parameter of the kernel was set as ⅓.

Results

PCS of Normal, Steatosis and Fibrosis Livers

Figures 8A, 8B, 8C, 8D, 8E, 8F, 8G, 8H, 8I:
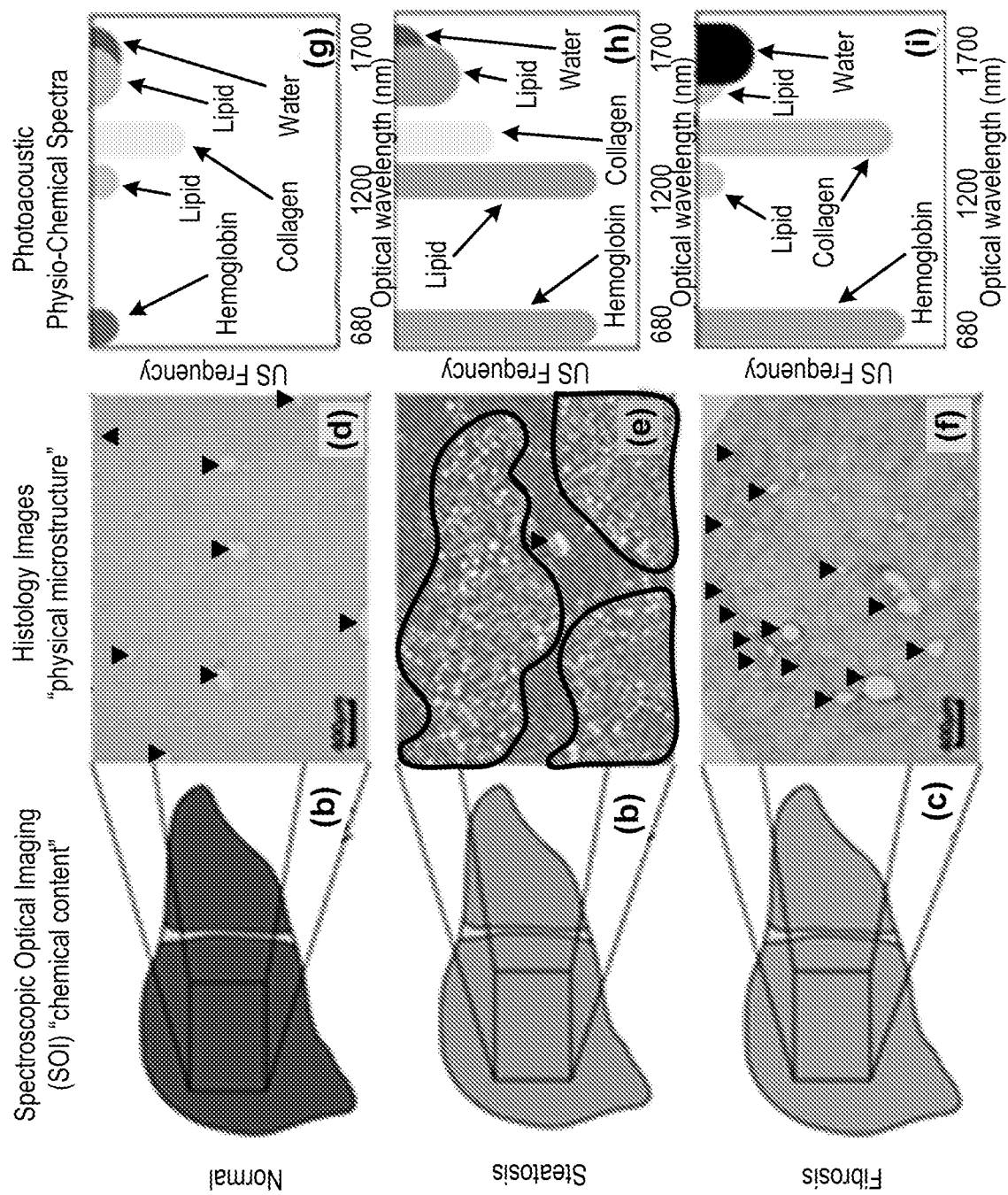
Figures 9F, 9G, 9H, 9I, 9J:
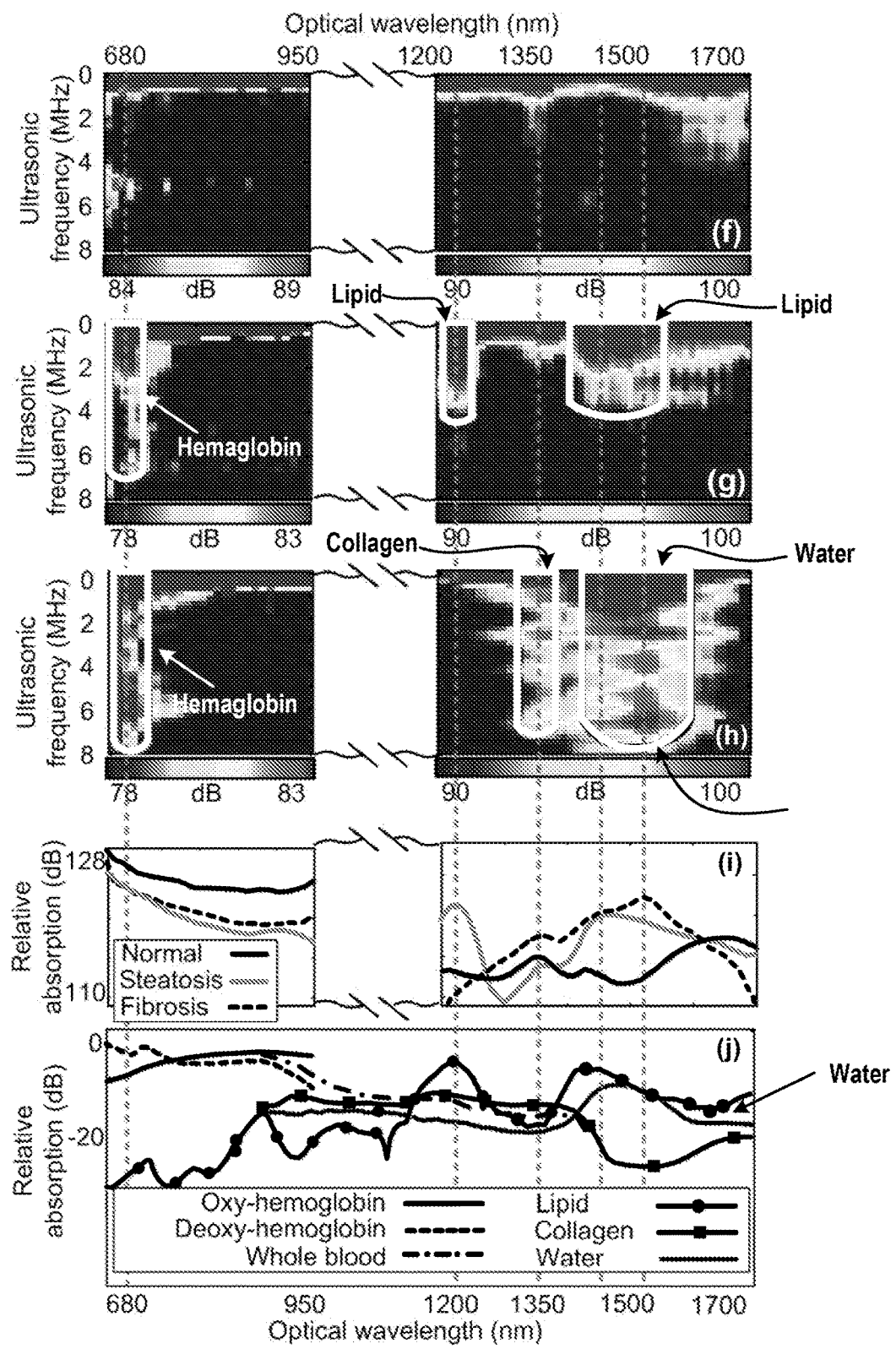

FIGS. 8(a)-8(i) schematically demonstrate the concept of PCS. Similar to SOI, the optical absorption or "colors" of the livers corresponding to their chemical components can be observed by PA signal amplitudes along the optical spectra. The microstructures of the liver tissues correlate to the frequency domain power distribution of the PA signals, as the heterogeneous distribution of the chemical components produces high frequency components in the signals. With more high frequency components, the power spectra appear extended along the US frequency axis, as shown by the vertical stripes in FIGS. 8(a)-8(i). By arranging the signal power spectra acquired along the optical-spectrum-of-interest side-by-side, the PCS in FIG. 8(g)-8(i) are formulated. Stripe features are expected at the absorption peaks of the chemical components. Such stripes are defined as a PCS fingerprint of a specific chemical component. Considering the difference in chemical components and microstructures, each liver condition should possess a unique combination of fingerprints. Based on optical spectra of the chemical components relevant to NAFLD (including hemoglobin, lipid, collagen and water, the optical absorption spectra of which are shown in FIGS. 9(e) and 9(j) and the histology images in FIGS. 8(d)-8(f), the hypothetic PCS of three typical liver conditions in FIGS. 8(g)-8(i) were derived. (1) In the normal liver in FIG. 8(d), the scattered, heterogeneous distribution of the collagen in the walls of the portal veins and bile ducts induces the extended collagen fingerprint in 1350-1390 nm in FIG. 8(g). (2) In the steatosis liver in FIG. 8(e), the scattered, heterogeneous deposition of the lipid increases extension of lipid fingerprints in 1200-1240 nm as well as 1400-1600 nm, and the hemoglobin fingerprint around 700 nm in FIG. 8(h). The increase of lipid induces the higher magnitude of lipid fingerprint. The decrease of blood content in the steatosis region lowers the magnitude of the hemoglobin fingerprint. (3) The changes in fibrosis liver in FIG. 8(f) include the deposition of collagen, the further loss of blood and the water content increase. The changes will be represented by the PCS as the extension and the higher magnitude of the collagen fingerprint in 1350-1390 nm and water fingerprint in 1500-1600 nm, in parallel to the extension and the lower magnitude of the hemoglobin fingerprint.

FIG. 9(a)-(c) shows the actual PCS of liver conditions including normal liver, a liver with extreme steatosis, and a liver with extreme fibrosis. The PCS map in the 680-950 nm range in FIGS. 9(a) and 9(f) is saturated to clearly show the weaker hemoglobin fingerprints in FIGS. 9(b) and 9(c). The hypothetic PCS agree with the actual PCS. By summing up the spectral amplitudes along each wavelength in normal scale, the overall amplitude of each fingerprint, or equivalently the absorption spectrum of each tissue sample, comparable to those in SOI, is shown in FIGS. 9(d) and 9(i). Note that both the steatosis and the fibrosis samples show broad fingerprints in the optical spectral range of 1400-1600 nm, where the absorption spectra of water and lipid partly overlap. Yet a close observation indicates that the broad fingerprint in the steatosis PCS reaches the peak magnitude at around 1450 nm due to the lipid deposition, whereas that in fibrosis reaches the peak magnitude at around 1540 nm due to the increase of water content.

Since the PCS in the 680-950 nm range in FIGS. 9(a) and 9(f) were saturated, the power spectra of the three tissue samples at 700 nm was plot in FIG. 12 for comparing their frequency component distributions. The normal liver tissue shows the largest overall spectral amplitudes due to the high blood content. The frequency components in the power spectra of normal liver decrease almost monotonically along the US frequencies, as the blood content homogeneously distributed in the liver sample. In the spectra of steatosis and fibrosis tissue, although the spectral amplitudes are lower, the amplitudes of the frequency components within 7-8 MHz are comparable to or even higher than those of the low frequency components below 2 MHz, as the lipid and collagen heterogeneously distributed in the liver samples.

Non-Invasive In Situ Imaging of Mouse Livers

The results in the previous section raise the possibility that the lipid and the collagen fingerprints could be the signature features to characterize extreme steatosis and fibrosis livers. The identification of these two liver conditions was attempted by in situ, non-invasive experiments. The setup and procedures are describes above in the method section. PASA was implemented to each A-line of the beam-formed PA signals for quantifying the lipid and collagen fingerprints at wavelengths of 1220 and 1370 nm, respectively.

FIG. 14(a) shows the results from an obese mouse with severe liver steatosis and its normal control. Because the linear array used (L7-4, Philips Healthcare, Andover, Mass.) covers the frequency range below 10 MHz, the image resolution is relatively low. Comparing to the PASA parameters of the normal liver tissue, the increase of lipid content in steatosis liver tissue lead to the increase of its spectral amplitude, and consequently the PASA parameters of intercept as well as the midband-fit. The heterogeneous distribution of the lipid droplets increased the extension of the lipid fingerprint, which is quantified as larger slope values. The contrasts in the spectral magnitudes (especially the intercept) between the normal live and liver with steatosis are not as prominent as those in the spectral slope. This is due to the fact that the fat deposited on the abdomen wall attenuated the light energy deliverable to the liver. The slope values in this case are more reliable given sufficient illumination power.

The US, PA images and the spectral parameters of normal and fibrosis mouse livers are shown in FIG. 14(b). The spectral amplitudes of the liver with fibrosis are higher than those of the normal liver due to the collagen deposition. The spectral slope values are larger than those of the normal tissue due to the heterogeneous distribution of the collagen fibers.

The fibrosis and normal livers were also compared at 700 nm, as shown in FIG. 15. Because the normal liver includes more blood content compared to the liver with fibrosis, its spectral amplitudes are higher. However, the heterogeneous deposition of collagen within the liver tissue induces the further extension of the hemoglobin fingerprint and equivalently higher slope values.

PCS of a Progressive NAFLD Model in Mice

Aside from extreme liver conditions, NAFLD also includes stages where steatosis and fibrosis co-exist in the liver. To further examine the sensitivity of the methods of the present disclosure to pathological changes in liver, a mouse model (STAM, Stelic Institute and Co., Tokyo, Japan) is used with a quick yet full spectrum of NAFLD progression. The PCS of a total of 9 mouse livers (3 normal, 3 with steatosis, and 3 with fibrosis, each scanned 4 times at different sections) were acquired. The representative PCS of the mouse livers at three conditions are shown in FIGS. 10(d)-10(f), 10(j)-10(l). The PCS are characterized by PASA at the absorption peaks of the three chemical contents relevant to the NAFLD, hemoglobin at 700 nm, lipid at 1220 nm, and collagen at 1370 nm. All of the PCS fingerprints in FIGS. 9(a)-9(j) are repeated in FIGS. 10(d)-10(f), 10(j)-10(l). A major difference between the PCS in FIGS. 10(d)-10(f), 10(j)-10(l) and FIGS. 9(a)-9(j) is that FIGS. 10(f), 10(l) show a weak but discernible lipid fingerprint in 1200-1240 nm. This result agrees with the histology image in FIGS. 10(c) and 10(i) where steatosis and fibrosis occur simultaneously at the early fibrosis stage of the STAM model.

Categorization of the Liver Conditions by Support Vector Machine (SVM)

The residual lipid in a liver with fibrosis, in addition to the quick progression of the steatosis and fibrosis, makes the liver conditions less distinguishable using PASA parameters at single wavelength or the fingerprint of one characteristic chemical component, as shown in the error-bar plots in FIGS. 13(a)-13(r). A multi-variant analysis tool, SVM is thereby introduced. Due to the overlap of water and lipid fingerprints in 1400 to 1600 nm, these two fingerprints were not considered in this example. The usage of the experiment data is described in the method section. Table 2 shows the prediction accuracy of the method by using either or both of the slope and midband-fit values. In this example, categorization with all PASA parameters gives the best diagnosis results. Categorization with slope values alone demonstrates significant advantage over that with amplitudes. FIG. 16 shows the categorization with slope values.

TABLE 2

SVM categorization

| | Categorization accuracy |
|---|---|
| With slope only | 92% (11/12) |
| With amplitude (midband-fit only) | 33% (4/12) |
| With both sloe and amplitude | 100% (12/12) |

The PCS includes rich diagnostic information of liver conditions and has shown repeatability of the same liver conditions by different pathogenesis. Currently the PCS are characterized by the PASA at specific wavelengths with SVM. The PASA method gives quick evaluation of the amplitudes and extensions of the fingerprints, which represent the concentration of the chemical components of the tissue samples and the dimensions of the chemical clusters, respectively. However, the linear approximation in PASA ignores the fluctuations in the signal power spectrum. As previously studied in USSA techniques, the periodically fluctuating patterns in the power spectra could be another representation of the cluster sizes or repetitive distributions of the backscatters. The observation at the limited number of wavelengths independently is sufficient for identifying the liver conditions in this study. However, the relative changes between the chemical components, such as the ratio of the extensions of the fingerprints, could contribute to more accurate evaluations of the disease conditions. The SVM is fundamentally a binary classifier, which could involve ambiguous decisions when extended to multi-classification tasks. Thus, the present disclosure is not limited to SVM, but rather further contemplates use of more comprehensive diagnostic information included in the PCS with more advanced analysis tools to better extract data.

The experimental results indicate the potential for the methods of the present disclosure in grading the severity of the liver conditions. For example, the trend of lipid content change during the NAFLD progression can be observed in both the slope and the midband-fit values in FIGS. 13(c), 13(i), 13(o) and 13(d), 13(j), 13(p). In addition, the collagen concentration change between non-fibrotic and fibrotic liver has also been quantitatively represented by the PASA parameters in FIGS. 13(e), 13(k), 13(q) and 13(f), 13(l), 13(r). The method could also be extended to the diagnosis of other NAFLD related conditions such as steatohepatitis and cirrhosis. The characteristic change in steatohepatitis is the formation of macrovesicular and inflammatory foci, composed predominantly of inflammation cells (including lymphocytes). Such focal structure can be captured in PCS by implementing fluorescence agents targeted at the lymphocytes. The cirrhosis induces further loss of hemoglobin, the escape of the lipid droplets, and the further deposition of the collagen in liver, all of which can be reflected by the change of the corresponding fingerprints in PCS. PAPCA could also be implemented in the diagnosis of kidney diseases, cardiovascular diseases, or cancer, where diffusive patterns of the chemical components can be found.

The feasibility of the non-invasive acquisition of PCS is validated in mice. As noted above, exemplary PA imaging depths can reach up to 5 cm by 800 nm laser. The light penetration near 1200 nm could be even deeper due to the lower scattering coefficient at longer optical wavelengths. However, as light energy attenuation varies along the optical spectrum, the amplitude of the power spectra might not be a reliable representation of the pathological changes in liver. The slope values could be more reliable, as demonstrated in most of the experiment results in this study.

Applications for PAPCA

As described above, PAPCA has been validated through various studies on mouse models of NAFLD, by combining PAI and US with PASA for characterizing optically absorbing microstructures in phantoms and biological tissues. Quantified spectral parameters from PAPCA can enable accurate characterization of progressive liver conditions, e.g., lipid infiltration in liver, and even quantify the dimension of macro- and microstructures, for example, lipid clusters, in subsurface tissue. Besides liver diseases, PAPCA will contribute to better diagnosis and management of many other diseases, such as cancer and inflammation, by offering a non-invasive, non-ionizing and cost-efficient imaging tool with previously unmatched sensitivity and specificity.

Needle biopsy is widely used in the diagnosis of diseases in organs such as breast, liver and prostate. Currently, biopsy procedures are mostly guided by US imaging, which, as mentioned previously, lacks reliability of identifying regions of diseased tissue. PAPCA, demonstrating prominent advantages over US imaging, may improve imaging guidance of needle biopsy. PAPCA can be achieved by delivering optical energy by an optical fiber and detecting the resulting PA signal by a needle hydrophone or an optical resonator based ultrasound detector such as a microring resonator. The optical fiber, needle hydrophone and microring could all be miniaturized to the dimensions of about a hundred microns and integrated at the tip of a biopsy needle.

PAPCA can also be beneficial for guiding biopsies. Conventional US-guided biopsies utilize two dimensional US images to help guide a biopsy needle through three dimensional tissue. Therefore, small and/or deep regions may be difficult to accurately target. As a result, multiple needle insertions and passes are often necessary before a desired tissue is successfully obtained. In contrast to conventional methods, the current technology provides for a PAPCA biopsy needle comprising a fiber optic light source and a US detector embedded within. The PAPCA biopsy needle can perform PA measurements as the needle is being inserted into tissue and simultaneously use PAPCA to determine the chemical and physical structures in front of the needle. This guided biopsy needle and method provides accurate targeting of biologic material, which increases the diagnostic accuracy and also decreases the number of biopsy attempts before a successful biopsy is performed. The PAPCA biopsy needle can be used to perform guided biopsies in various tissues. Non-limiting examples of tissues that the PAPCA biopsy needle can be guided through include breast, prostate, liver, and thyroid.

A needle probe in accordance with certain aspects of the present disclosure can be placed into or next to a target tissue for evaluation of regional conditions without performing a biopsy. An exemplary needle probe 100 is shown in FIG. 17. The needle probe 100 defines a longitudinal body 110 that defines an outer surface 112 and an inner longitudinal core 114. The longitudinal body 110 is composed of any material used in the art, such as, for example, metal, steel, or stainless steel. The inner longitudinal core 114 is hollow or substantially hollow, such that the longitudinal core 114 is configured to receive various elements as described further below. Although other shapes can be employed, in various embodiments, the longitudinal body 110 is cylindrical, i.e., has a circular cross-sectional geometry. The longitudinal body 110 terminates in a tip 120, so as to define the needle probe 100. The needle probe 100 includes a side-firing optical fiber 122 (coupled at one end to a laser, not shown) extending longitudinally within the longitudinal core 114. The needle probe 100 also includes a miniaturized hydrophone 124 positioned within the longitudinal core 114, parallel or adjacent to the side-firing optical fiber 122. In certain embodiments, the needle probe 100 has an outer diameter of greater than or equal to about 7 gauge (4.572 mm) to less than or equal to about 34 gauge (0.1842 mm), and an inner diameter D, i.e., diameter of the hollow longitudinal core 114, of greater than or equal to about 0.2 mm to less than or equal to less than or equal to about 1.5 mm. The side firing optical fiber 122 may have a diameter of greater than or equal to about 0.2 mm to less than or equal to about 2 mm. The miniaturized hydrophone 124 may have a center frequency of greater than about 50 to less than or equal to about 500 MHz, a bandwidth of greater than or equal to about 50% to less than or equal to about 75%, and a diameter of greater than or equal to about 0.05 mm to less than or equal to about 1 mm. The size of the side-firing optical fiber 122 and hydrophone 124 are limited in dimension so that they both are smaller than an inner diameter D of the longitudinal core 114. In one embodiment, the needle probe 100 has an outer diameter of 18 gauge (1.27 mm), an inner longitudinal core 114 diameter of about 0.8 mm, the side firing optical fiber 122 has a diameter of about 0.5 mm, and the miniaturized hydrophone 124 has a center frequency of about 200 MHz, a bandwidth of about 60%, and a diameter of about 0.3 mm.

A window 130 extends longitudinally along the probe longitudinal body 110 from a first end 132 at or near the tip 120, for example, at the tip 120 or at a distance of greater than or equal to about 0.5 mm to less than or equal to about 5 mm from the tip 120, to a second end 134 that defines a predetermined distance designated "L" from the first end 132. The predetermined length L of the window 130 can be greater than or equal to about 5 mm to less than or equal to about 25 mm. In one embodiment, the length "L" of the window 130 is about 15 mm. The window 130 can be composed of any material used in the art that transmits light and sound, such as, for example, glass or plastic. Whereas the side-firing optical fiber 122 extends through the entire needle probe 100, i.e., to the tip 120, the hydrophone 124 is positioned at or near the second end 134 of the window 130, that is the end that is furthest from the tip 120. This arrangement helps to ensure that the hydrophone 124 will detect signals generated from tissue targeted by the optical fiber 122. The window 130 allows light to transfer from the optical fiber 122 to permit both light illumination on a target tissue and PA signal detection from the tissue. The outer surface 112 of the needle probe 100 may be colored white, for example, by painting, thus preventing PA signals generated on the longitudinal body 110.

The side-firing optical fiber 122 creates a cylindrical light source. Collectively, the side-firing optical fiber 122 and the window 130 provide a side-viewing arrangement that is different from designs where light is delivered from the tip of a fiber forming a point optical source. Due to the strong attenuation of light in biological tissues, a point source cannot generate PA signals with sufficient temporal length statistics-based power spectrum analysis. The cylindrical light source (formed by the side-firing optical fiber 122 and window 130) illuminates a large volume of tissue and generates temporally longer PA signals, relative to point optical sources, for more reliable PASA.

In use, the needle probe may be inserted into an organism and positioned in or adjacent to an anatomical feature of interest (e.g., into a target region of tissue). For example, in some embodiments, the needle probe is inserted through the skin and fat pad of an organism and then positioned such that the window is either in the liver, following conventional needle biopsy, or immediately above or adjacent to the liver surface. Although a connective tissue capsule covers the surface of a liver, the capsule is not problematic because it is both thin (70-100 μm) and optically and ultrasonically transparent. When the probe is in place, the laser is operated and a PCS spectrogram over an optical spectrum is acquired.

FIGS. 18(a)-18(d) show the results of a study of mouse livers performed with a probe according to the present technology. The probe of the study has an outer diameter of 18 gauge (1.27 mm), an inner core diameter of about 0.8 mm, a side firing optical fiber with a diameter of about 0.5 mm, a miniaturized hydrophone with a center frequency of about 200 MHz, a bandwidth of about 60%, and a diameter of about 0.3 mm, and a window with a length L of 15 mm. A laser light with 6 mJ per pulse is coupled into the side-firing fiber, formulating a light fluence of 13 mJ/cm$^2$ (within the ANSI safety limit) at the surface of the detection widow. When the probe is positioned at the target location (the liver), acquisition of PCS spectrogram over the optical spectrum of 680-1800 nm is conducted. FIG. 18(a) is a photograph of a light illumination pattern provided by the side-firing fiber optic. FIG. 18(b) is a schematic illustration of the probe inserted into the mouse liver such that the fiber optic illuminates a location within the liver and the hydrophone detects the signal generated therefrom. FIG. 18(c) is a PASA of signals generated from a normal and fatty liver, respectively. For each sample, the slope of the linear fit is computed by tan(θ). FIG. 18(d) shows quantified slope values form 12 fatty liver specimens versus 12 normal controls.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of assessing physical and chemical biomarkers in a tissue comprising:
   a. performing a photoacoustic scan by illuminating the tissue and detecting acoustic signals generated therefrom;
   b. transforming the acoustic signals into frequency domains to create a plurality of power spectra; and
   c. generating a two dimensional (2D) physio-chemical spectrogram (PCS) from the power spectra acquired from the photoacoustic scan.

2. The method according to claim 1, wherein the photoacoustic scan is performed over a range of wavelengths.

3. The method according to claim 1, wherein the illuminating the tissue is performed by a pulsed laser.

4. The method according to claim 3, wherein the pulsed laser has a tuning range that covers a strong absorption range of hemoglobin in near-infrared and vibrational absorption peaks of lipid, collagen and water.

5. The method according to claim 4, wherein the pulsed laser is tuned for two distinct ranges of wavelengths, including in a first range of wavelengths of greater than or equal to about 680 nm to less than or equal to about 950 nm and in a second range of wavelengths of greater than or equal to about 1200 nm to less than or equal to about 1700 nm.

6. The method according to claim 5, wherein the photoacoustic scan has a tuning step size of about 10 nm.

7. The method according to claim 6, wherein an energy output in a first range of wavelengths and a second range of wavelengths is greater than or equal to about 15 to less than or equal to about 20 mJ per pulse from the pulsed laser, and each pulse has a duration of about 8 ns.

8. The method according to claim 1, further comprising analyzing the power spectra by photoacoustic spectrum analysis (PASA), wherein the analyzing the power spectra by PASA comprises:
   a. fitting the power spectra to a linear model;
   b. extracting intercept, midband-fit, and slope values from the linear model; and
   c. quantifying a magnitude of the power spectra from the intercept and midband-fit values, and a frequency component distribution from the slope.

9. The method according to claim 1, wherein the tissue is liver tissue.

10. A method of assessing physical and chemical biomarkers in tissue of a liver, comprising:
    a. illuminating a first region of the liver with a pulsed laser in two distinct ranges of wavelengths, including a first wavelength range of greater than or equal to about 680 nm to less than or equal to about 950 nm and a second wavelength range of greater than or equal to about 1200 nm to less than or equal to about 1700 nm;
    b. detecting photoacoustic signals generated by the first region of the liver at each of the first wavelength range and the second wavelength range;
    c. transforming the photoacoustic signals into a frequency domain to create power spectra; and
    d. generating a two dimensional (2D) physio-chemical spectrogram (PCS) map from the power spectra.

11. The method according to claim 10, wherein an energy output in each respective first wavelength range and second wavelength range is greater than or equal to about 15 to less than or equal to about 20 mJ per pulse from the pulsed laser, and each pulse from the pulsed laser has a duration of about 8 ns.

12. The method according to claim 10, wherein the two dimensional PCS comprises a first axis representing an optical spectrum and a second axis representing an ultrasonic frequency.

13. The method according to claim 10, wherein the illuminating occurs at wavelengths of 700 nm, 1220 nm, and 1370 nm and a slope value and a midband-fit value are extracted from the wavelengths of 700 nm, 1220 nm, and 1370 nm by photoacoustic spectrum analysis.

14. The method according to claim 10, wherein the two dimensional PCS contains diagnostic information and enables quantitative analysis of concentrations and spatial distributions of chemical components in the liver.

15. The method according to claim 14, wherein the chemical components comprise hemoglobin, lipid, collagen, water, or combinations thereof.

16. The method according to claim 10, wherein the method is used to determine a condition of the tissue of the liver selected from a group consisting of: a normal liver condition, a liver having non-alcoholic fatty liver disease, and a liver having fibrosis.

17. A method of performing photoacoustic physio-chemical analysis (PAPCA), comprising:
    a. performing a plurality of photoacoustic scans on a tissue to generate a plurality of photoacoustic signals, wherein each photoacoustic scan comprises a range of wavelengths;
    b. transforming the plurality of photoacoustic signals at each wavelength into a frequency domain to create power spectra; and
    c. generating a two dimensional (2D) physio-chemical spectrogram (PCS) from the power spectra, wherein the PCS comprises a first axis representing an optical wavelength and a second axis representing ultrasonic frequency, wherein the optical wavelength indicates the chemical components in the tissue, and the ultrasonic frequency indicates the micron scale features of the tissue.

18. The method according to claim 17, wherein the PAPCA provides information about physical and biological biomarkers within the tissue.

19. The method according to claim 18, wherein the tissue is a liver in a subject.

20. The method according to claim 19, wherein the PAPCA is performed to determine whether the subject has non-alcoholic fatty liver disease or liver fibrosis.

* * * * *